US012642981B2

(12) United States Patent
Finch et al.

(10) Patent No.: US 12,642,981 B2
(45) Date of Patent: Jun. 2, 2026

(54) WCD PACING PULSE GENERATION

(71) Applicant: West Affum Holdings DAC, Dublin (IE)

(72) Inventors: David P. Finch, Bothell, WA (US); Leo J. Gilbert, Kirkland, WA (US); Joseph L. Sullivan, Kirkland, WA (US); Jaeho Kim, Redmond, WA (US); John Wei-Hao Huang, Bothell, WA (US); Brian J. Bennett, Redmond, WA (US); Kenneth F. Cowan, Everett, WA (US)

(73) Assignee: West Affum Holdings DAC, Dublin (IE)

( * ) Notice: Subject to any disclaimer, the term of this patent is extended or adjusted under 35 U.S.C. 154(b) by 290 days.

(21) Appl. No.: 18/446,391

(22) Filed: Aug. 8, 2023

(65) Prior Publication Data

US 2024/0139531 A1 May 2, 2024

Related U.S. Application Data

(60) Provisional application No. 63/420,523, filed on Oct. 28, 2022.

(51) Int. Cl.
*A61N 1/39* (2006.01)

(52) U.S. Cl.
CPC ......... *A61N 1/3912* (2013.01); *A61N 1/3904* (2017.08); *A61N 1/3937* (2013.01); *A61N 1/3987* (2013.01)

(58) Field of Classification Search
CPC .. A61N 1/3912; A61N 1/3904; A61N 1/3937; A61N 1/3987; A61N 1/046; A61N 1/0484
See application file for complete search history.

(56) References Cited

U.S. PATENT DOCUMENTS 3,724,355 A   4/1973 Busch et al.
3,724,455 A   4/1973 Unger
(Continued)

FOREIGN PATENT DOCUMENTS

DE      2005060985 A2   6/2007
EP        2305110 A1    4/2011
(Continued)

OTHER PUBLICATIONS

Heartstart MRx and XL AED Algorithm-Application Note, Jul. 2011, Edition 2 Philips Healthcare, USA.
(Continued)

*Primary Examiner* — Joseph M Dietrich
(74) *Attorney, Agent, or Firm* — Seed Intellectual Property Law Group LLP

(57) ABSTRACT

Apparatus and methods for generating pulse pacing in a wearable cardioverter defibrillator ("WCD"). In one aspect the WCD circuitry includes a power source such as a battery coupled to a charger that provides charge energy to an energy storage module. Control circuitry is operatively coupled to the charger and the output circuitry, and configured to cause the WCD circuitry to generate pacing pulses delivered to therapy electrodes (attached to an ambulatory patient) without a current source. The WCD circuitry includes one or more processing elements that are used to execute instructions provided by one or more software modules that are configured to support various functionality, including controlling generation of pacing pulses.

23 Claims, 16 Drawing Sheets

(56) References Cited

U.S. PATENT DOCUMENTS

| | | | |
|---|---|---|---|
| 4,583,524 A | 4/1986 | Hutchins |
| 4,619,265 A | 10/1986 | Morgan et al. |
| 4,666,432 A | 5/1987 | McNeish et al. |
| 4,698,848 A | 10/1987 | Buckley |
| 4,928,690 A | 5/1990 | Heilman et al. |
| 4,955,381 A | 9/1990 | Way et al. |
| 5,078,134 A | 1/1992 | Heilman et al. |
| 5,228,449 A | 7/1993 | Christ et al. |
| 5,348,008 A | 9/1994 | Bornn et al. |
| 5,353,793 A | 10/1994 | Bornn |
| RE34,800 E | 11/1994 | Hutchins |
| 5,394,892 A | 3/1995 | Kenny et al. |
| 5,405,362 A | 4/1995 | Kramer et al. |
| 5,429,593 A | 7/1995 | Matory |
| 5,474,574 A | 12/1995 | Payne et al. |
| 5,618,208 A | 4/1997 | Crouse et al. |
| 5,662,690 A | 9/1997 | Cole et al. |
| 5,708,978 A | 1/1998 | Johnsrud |
| 5,741,306 A | 4/1998 | Glegyak et al. |
| 5,782,878 A | 7/1998 | Morgan et al. |
| 5,792,204 A | 8/1998 | Snell |
| 5,902,249 A | 5/1999 | Lyster |
| 5,913,685 A | 6/1999 | Hutchins |
| 5,944,669 A | 8/1999 | Kaib |
| 6,047,203 A | 4/2000 | Sackner et al. |
| 6,065,154 A | 5/2000 | Hulings et al. |
| 6,108,197 A | 8/2000 | Janik |
| 6,148,233 A | 11/2000 | Owen et al. |
| 6,201,992 B1 | 3/2001 | Freeman |
| 6,263,238 B1 | 7/2001 | Brewer et al. |
| 6,280,461 B1 | 8/2001 | Glegyak et al. |
| 6,287,328 B1 | 9/2001 | Snyder et al. |
| 6,304,780 B1 | 10/2001 | Owen et al. |
| 6,319,011 B1 | 11/2001 | Motti et al. |
| 6,334,070 B1 | 12/2001 | Nova et al. |
| 6,356,785 B1 | 3/2002 | Snyder et al. |
| 6,427,083 B1 | 7/2002 | Owen et al. |
| 6,437,083 B1 | 8/2002 | Brack et al. |
| 6,450,942 B1 | 9/2002 | Lapanashvili et al. |
| 6,529,875 B1 | 3/2003 | Nakajima et al. |
| 6,546,285 B1 | 4/2003 | Owen et al. |
| 6,671,545 B2 | 12/2003 | Fincke |
| 6,681,003 B2 | 1/2004 | Linder et al. |
| 6,762,917 B1 | 7/2004 | Verbiest et al. |
| 7,065,401 B2 | 6/2006 | Worden |
| 7,099,715 B2 | 8/2006 | Korzinov |
| 7,212,850 B2 | 5/2007 | Prystowsky |
| 7,559,902 B2 | 7/2009 | Ting et al. |
| 7,587,237 B2 | 9/2009 | Korzinov |
| 7,753,759 B2 | 7/2010 | Pintor et al. |
| 7,865,238 B2 | 1/2011 | Brink |
| 7,870,761 B2 | 1/2011 | Valentine et al. |
| 7,907,996 B2 | 3/2011 | Prystowsky |
| 7,941,207 B2 | 5/2011 | Korzinov |
| 7,974,689 B2 | 7/2011 | Volpe et al. |
| 8,024,037 B2 | 9/2011 | Kumar |
| 8,135,462 B2 | 3/2012 | Owen et al. |
| 8,140,154 B2 | 3/2012 | Donnelly et al. |
| 8,369,944 B2 | 2/2013 | Macho et al. |
| 8,527,028 B2 | 9/2013 | Kurzweil et al. |
| 8,548,557 B2 | 10/2013 | Garstka et al. |
| 8,560,044 B2 | 10/2013 | Kurzweil et al. |
| 8,615,295 B2 | 12/2013 | Savage et al. |
| 8,644,925 B2 | 2/2014 | Volpe et al. |
| 8,676,313 B2 | 3/2014 | Volpe et al. |
| 8,706,255 B2 | 4/2014 | Phillips et al. |
| 8,742,349 B2 | 6/2014 | Urbon et al. |
| 8,897,860 B2 | 11/2014 | Volpe et al. |
| 8,904,214 B2 | 12/2014 | Volpe et al. |
| 8,965,500 B2 | 2/2015 | Macho et al. |
| 9,008,801 B2 | 4/2015 | Kaib et al. |
| 9,084,583 B2 | 7/2015 | Mazar et al. |
| 9,089,685 B2 | 7/2015 | Sullivan et al. |
| 9,119,547 B2 | 9/2015 | Cazares et al. |
| 9,131,901 B2 | 9/2015 | Volpe et al. |
| 9,132,267 B2 | 9/2015 | Kaib |
| 9,265,432 B2 | 2/2016 | Warren et al. |
| 9,345,898 B2 | 5/2016 | Piha et al. |
| 9,408,548 B2 | 8/2016 | Volpe et al. |
| 9,445,719 B2 | 9/2016 | Libbus et al. |
| 9,454,219 B2 | 9/2016 | Volpe et al. |
| 9,579,020 B2 | 2/2017 | Libbus et al. |
| 9,592,403 B2 | 3/2017 | Sullivan |
| 9,598,799 B2 | 3/2017 | Shoshani et al. |
| 9,675,804 B2 | 6/2017 | Whiting et al. |
| 9,724,008 B2 | 8/2017 | Sullivan et al. |
| 9,757,581 B2 | 9/2017 | Sullivan et al. |
| 9,878,171 B2 | 1/2018 | Kaib |
| 9,895,105 B2 | 2/2018 | Romem |
| 9,901,741 B2 | 2/2018 | Chapman et al. |
| RE46,926 E | 7/2018 | Bly et al. |
| 10,016,613 B2 | 7/2018 | Kavounas |
| 10,076,656 B2 | 9/2018 | Dar et al. |
| 10,192,387 B2 | 1/2019 | Brinig et al. |
| 10,307,133 B2 | 6/2019 | Kaib |
| 10,463,867 B2 | 11/2019 | Kaib et al. |
| 10,589,110 B2 | 3/2020 | Oskin et al. |
| 10,599,814 B2 | 3/2020 | Landrum et al. |
| 11,058,885 B2 | 7/2021 | Kim |
| 11,278,731 B2 | 3/2022 | Foshee, Jr. et al. |
| 11,471,693 B1 | 10/2022 | Sullivan |
| 2002/0181680 A1 | 12/2002 | Linder et al. |
| 2003/0158593 A1 | 8/2003 | Heilman et al. |
| 2005/0107833 A1 | 5/2005 | Freeman et al. |
| 2005/0107834 A1 | 5/2005 | Freeman et al. |
| 2006/0173499 A1 | 8/2006 | Hampton et al. |
| 2008/0312709 A1 | 12/2008 | Vollpe et al. |
| 2009/0005827 A1 | 1/2009 | Weintraub et al. |
| 2010/0007413 A1 | 1/2010 | Herleikson et al. |
| 2010/0298899 A1 | 11/2010 | Donnelly et al. |
| 2011/0022105 A9 | 1/2011 | Owen et al. |
| 2011/0288604 A1 | 11/2011 | Kaib et al. |
| 2011/0288605 A1 | 11/2011 | Kaib et al. |
| 2012/0112903 A1 | 5/2012 | Kaib et al. |
| 2012/0144551 A1 | 6/2012 | Guldalian |
| 2012/0150008 A1 | 6/2012 | Kaib et al. |
| 2012/0158075 A1 | 6/2012 | Kaib et al. |
| 2012/0191476 A1 | 7/2012 | Reid et al. |
| 2012/0265265 A1 | 10/2012 | Razavi et al. |
| 2012/0283794 A1 | 11/2012 | Kaib et al. |
| 2012/0293323 A1 | 11/2012 | Kaib et al. |
| 2012/0302860 A1 | 11/2012 | Volpe et al. |
| 2012/0310315 A1 | 12/2012 | Savage et al. |
| 2013/0085538 A1 | 4/2013 | Volpe et al. |
| 2013/0144355 A1 | 6/2013 | Macho et al. |
| 2013/0231711 A1 | 9/2013 | Kaib |
| 2013/0245388 A1 | 9/2013 | Rafferty et al. |
| 2013/0274565 A1 | 10/2013 | Langer et al. |
| 2013/0317852 A1 | 11/2013 | Worrell et al. |
| 2013/0325078 A1 | 12/2013 | Whiting et al. |
| 2014/0012144 A1 | 1/2014 | Crone |
| 2014/0025131 A1 | 1/2014 | Sullivan et al. |
| 2014/0043149 A1 | 2/2014 | Cowan et al. |
| 2014/0046391 A1 | 2/2014 | Cowan et al. |
| 2014/0070957 A1 | 3/2014 | Longinotti-Buitoni et al. |
| 2014/0163663 A1 | 6/2014 | Poddar et al. |
| 2014/0324112 A1 | 10/2014 | Macho et al. |
| 2014/0378812 A1 | 12/2014 | Saroka et al. |
| 2015/0039053 A1 | 2/2015 | Kaib et al. |
| 2015/0161554 A1 | 6/2015 | Sweeney et al. |
| 2015/0297135 A1 | 10/2015 | Shoshani et al. |
| 2015/0328472 A1 | 11/2015 | Sullivan et al. |
| 2016/0004831 A1 | 1/2016 | Carlson et al. |
| 2016/0076175 A1 | 3/2016 | Rock et al. |
| 2016/0076176 A1 | 3/2016 | Rock et al. |
| 2016/0082277 A1 | 3/2016 | Foshee, Jr. et al. |
| 2016/0113581 A1 | 4/2016 | Amir et al. |
| 2016/0256104 A1 | 9/2016 | Romem et al. |
| 2016/0283900 A1 | 9/2016 | Johnson et al. |
| 2017/0014073 A1 | 1/2017 | Shoshani et al. |
| 2017/0027469 A1 | 2/2017 | Amir et al. |
| 2017/0036066 A1 | 2/2017 | Chahine |
| 2017/0040758 A1 | 2/2017 | Amir et al. |
| 2017/0056682 A1 | 3/2017 | Kumar et al. |

(56) References Cited

U.S. PATENT DOCUMENTS

| | | | |
|---|---|---|---|
| 2017/0162840 A1 | 6/2017 | Pendry | |
| 2017/0319862 A1 | 11/2017 | Foshee, Jr. et al. | |
| 2017/0367591 A1 | 12/2017 | Jorgensen | |
| 2018/0116537 A1 | 5/2018 | Sullivan et al. | |
| 2018/0117299 A1 | 5/2018 | Gustavson et al. | |
| 2018/0184933 A1 | 7/2018 | Sullivan et al. | |
| 2018/0185662 A1 | 7/2018 | Foshee, Jr. et al. | |
| 2018/0243578 A1 | 8/2018 | Volosin | |
| 2018/0361165 A1 | 12/2018 | Jaax et al. | |
| 2019/0030352 A1 | 1/2019 | Sullivan et al. | |
| 2019/0076666 A1 | 3/2019 | Medema | |
| 2019/0116896 A1 | 4/2019 | Armour et al. | |
| 2019/0321650 A1 | 10/2019 | Raymond et al. | |
| 2020/0398065 A1* | 12/2020 | Engman | A61N 1/3925 |
| 2021/0052180 A1 | 2/2021 | Kim | |

FOREIGN PATENT DOCUMENTS

| | | | |
|---|---|---|---|
| JP | 2005507747 A | 3/2005 |
| JP | 2014500099 A | 1/2014 |
| JP | 2014526282 A | 10/2014 |
| WO | 9839061 A2 | 9/1998 |
| WO | 2011/146448 A1 | 11/2011 |
| WO | 2012/064604 A1 | 5/2012 |
| WO | 2012/151160 A1 | 11/2012 |
| WO | 2015/056262 A1 | 4/2015 |

OTHER PUBLICATIONS

Klein, H. U., Goldenberg, I., and Moss, A. J., "Risk Stratification for Implantable Cardioverter Defibrillator Therapy: The Role of the Wearable Cardioverter-Defibrillator, Clinical update," European Heart Journal, May 31, 2013, pp. 1-14, doi:10.1093/eurheartj/eht167, European Society of Cardiology.

LIFECOR LifeVest System Model WCD 3100 Operator's Manual, 2006, PN 20B0040 Rev FI, Zoll Lifecor Corporation, Pittsburgh, PA.

LifeVest Model 4000 Patient Manual, Zoll, 2009, PN 20B0047 Rev B.

Pagan-Carlo, et al., "Encircling Overlapping Multipulse Shock Waveforms for Transthoracic Defibrillation," JACC Journals, Dec. 1998, vol. 32 Issue 7, p. 2065-2071.

The LifeVest Network/Patient Data Management System, Zoll, 2015, 20C0503 Rev A.

Zoll, LifeVest, Proven protection from Sudden Cardiac Death, issued Mar. 27, 2018, 4 pages. Pittsburgh PA, USA.

International Search Report and Written Opinion for PCT Application No. PCT/US2015/051726, dated May 20, 2016, European Patent Office, Rijswijk, 11 pages.

* cited by examiner

82

170

180
OUTSIDE
MONITORING
DEVICE 104    85

111

105

108

100
UNIT

High Side Gate Drive Circuit

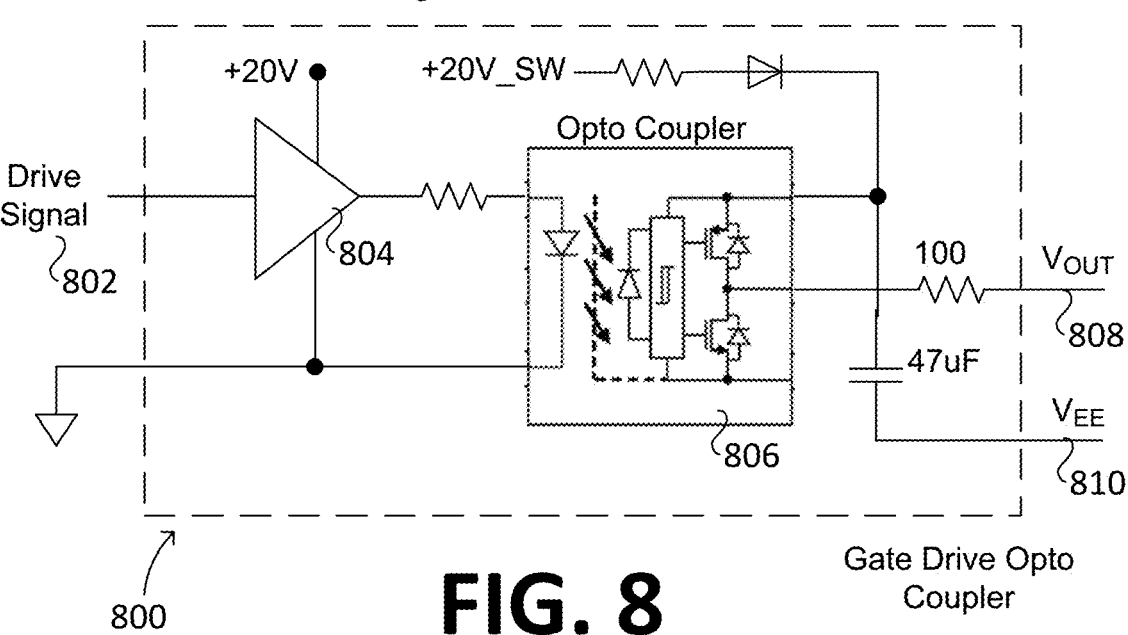

Drive
Signal
802

804

Opto Coupler

806

+20V

+20V_SW

100

47uF

V<sub>OUT</sub>
808

V<sub>EE</sub>
810

Gate Drive Opto
Coupler

Controller

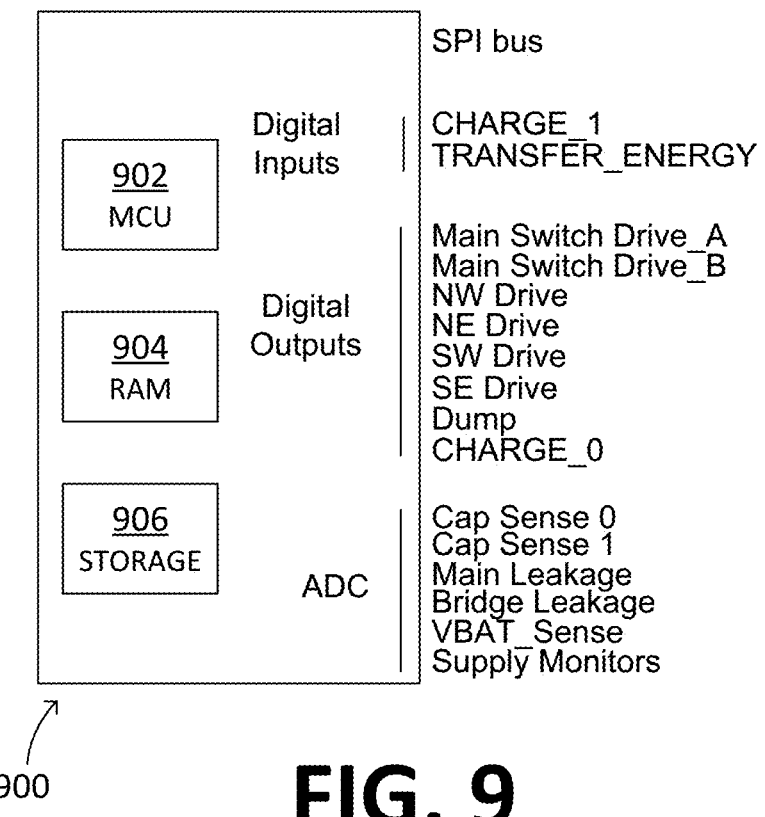

SPI bus

Digital
Inputs

CHARGE_1
TRANSFER_ENERGY

Digital
Outputs

Main Switch Drive_A
Main Switch Drive_B
NW Drive
NE Drive
SW Drive
SE Drive
Dump
CHARGE_0

ADC

Cap Sense 0
Cap Sense 1
Main Leakage
Bridge Leakage
VBAT_Sense
Supply Monitors

902
MCU

904
RAM

906
STORAGE

Configure Charger to Operate as
Current Source

1002

Generate initial Pulses using an Initial
Voltage based on Default Impedance

1004

Measure Impedance at
selected point in Pulse

1006

Use Measured Impedance and
Voltage to Adjust Charger Output

1008

1300

Measure Patient Impedance

1302

Determine the Charge Voltage ($V_{charge}$)

1304

Deliver Pacing Pulse with Output Switch(s) in Linear Mode

1306

| Pace Pulse Options Value | Pace Pulse Duty Cycle Pattern, 200 uS per entry | | | | | | | | | | | | | | | | Duty Cycle % | Duty Cycle Pattern Hex Code |
|---|---|---|---|---|---|---|---|---|---|---|---|---|---|---|---|---|---|---|
| | 0 | 1 | 2 | 3 | 4 | 5 | 6 | 7 | 8 | 9 | 10 | 11 | 12 | 13 | 14 | 15 | | |
| 16 | 1 | 1 | 1 | 1 | 1 | 1 | 1 | 1 | 1 | 1 | 1 | 1 | 1 | 1 | 1 | 1 | 100.0% | 0xFFFF |
| 15 | 0 | 1 | 1 | 1 | 1 | 1 | 1 | 1 | 1 | 1 | 1 | 1 | 1 | 1 | 1 | 1 | 93.8% | 0xFFFE |
| 14 | 0 | 1 | 1 | 1 | 1 | 1 | 1 | 1 | 0 | 1 | 1 | 1 | 1 | 1 | 1 | 1 | 87.5% | 0xFEFE |
| 13 | 0 | 1 | 1 | 1 | 1 | 0 | 1 | 1 | 1 | 1 | 0 | 1 | 1 | 1 | 1 | 1 | 81.3% | 0xFBDE |
| 12 | 0 | 1 | 1 | 1 | 0 | 1 | 1 | 1 | 0 | 1 | 1 | 1 | 0 | 1 | 1 | 1 | 75.0% | 0xEEEE |
| 11 | 0 | 1 | 1 | 1 | 0 | 1 | 1 | 0 | 1 | 1 | 0 | 1 | 1 | 0 | 1 | 1 | 68.8% | 0xDB6E |
| 10 | 0 | 1 | 0 | 1 | 0 | 1 | 1 | 0 | 1 | 1 | 0 | 1 | 1 | 0 | 1 | 1 | 62.5% | 0xDB6A |
| 9 | 0 | 1 | 0 | 1 | 0 | 1 | 1 | 0 | 1 | 1 | 0 | 1 | 0 | 1 | 0 | 1 | 56.3% | 0xAB6A |
| 8 | 0 | 1 | 0 | 1 | 0 | 1 | 0 | 1 | 0 | 1 | 0 | 1 | 0 | 1 | 0 | 1 | 50.0% | 0xAAAA |
| 7 | 0 | 1 | 0 | 1 | 0 | 0 | 1 | 0 | 1 | 0 | 1 | 0 | 1 | 0 | 0 | 1 | 43.8% | 0x954A |
| 6 | 0 | 0 | 1 | 0 | 0 | 1 | 0 | 0 | 1 | 0 | 1 | 0 | 1 | 0 | 0 | 1 | 37.5% | 0x9524 |
| 5 | 0 | 0 | 0 | 1 | 0 | 0 | 1 | 0 | 0 | 1 | 0 | 0 | 1 | 0 | 0 | 1 | 31.3% | 0x9248 |
| 4 | 0 | 0 | 0 | 1 | 0 | 0 | 0 | 1 | 0 | 0 | 0 | 1 | 0 | 0 | 0 | 1 | 25.0% | 0x8888 |
| 3 | 0 | 0 | 0 | 0 | 0 | 1 | 0 | 0 | 0 | 0 | 1 | 0 | 0 | 0 | 0 | 1 | 18.8% | 0x8420 |
| 2 | 0 | 0 | 0 | 0 | 0 | 0 | 0 | 1 | 0 | 0 | 0 | 0 | 0 | 0 | 0 | 1 | 12.5% | 0x8080 |
| 1 | 0 | 0 | 0 | 0 | 0 | 0 | 0 | 0 | 0 | 0 | 0 | 0 | 0 | 0 | 0 | 1 | 6.3% | 0x8000 |

WCD PACING PULSE GENERATION

CROSS-REFERENCE TO RELATED APPLICATIONS

This patent application claims priority from U.S. provisional patent application Ser. No. 63/420,523, filed Oct. 28, 2022, which is incorporated herein in its entirety for all purposes.

NOTICE OF MATERIALS SUBJECT TO COPYRIGHT PROTECTION

Portions of the material in this patent document are subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, and for patent-related purposes only, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND INFORMATION

A wearable medical system ("WMS") is an advanced form of a medical system. A WMS typically includes one or more wearable components that a patient can wear or carry, and possibly other components that can be portable, or stationary such as base station and/or an electric charger. The WMS may also include one or more associated software packages, such as software applications ("apps"), which can be hosted by the wearable component, and/or by a mobile device, and/or by a remote computer system that is accessible via a communications network such as the internet, and so on.

A WMS typically includes one or more sensors that can sense when a parameter of the patient is problematic, and cause the WMS to initiate an appropriate action. The appropriate action could be for the WMS to communicate with the patient or even with a bystander, to transmit an alert to a remotely located clinician, and to even administer treatment or therapy to the patient by itself. The one or more sensors may sense more than one parameter of the patient. The multiple parameters may be used for determining whether or not to administer the treatment or therapy, or be suitable for detecting different problems and/or for administering respectively different treatments or therapies to the patient.

A WMS may also include the appropriate components for implementing a wearable cardioverter defibrillator ("WCD"), a pacemaker, and so on. Such a WMS can be for patients who have an increased risk of sudden cardiac arrest ("SCA"). In particular, when people suffer from some types of heart arrhythmias, the result may be that blood flow to various parts of the body is reduced. Some arrhythmias may result in SCA, which can lead to death very quickly, unless treated within a short time. Some observers may have thought that SCA is the same as a heart attack, but it is not. For such patients, an external cardiac defibrillator can deliver a shock through the heart to restore its normal rhythm. The problem is that it is hard for an external cardiac defibrillator to be brought to the patient within that short time. One solution, therefore, is for such patients to be given a WMS that implements a WCD. This solution is at least temporary and, after a while, such as two months, the patient may instead receive a surgically implantable cardioverter defibrillator ("ICD"), which would then become a permanent solution.

A WMS that implements a WCD typically includes a harness, vest, belt, or other garment that the patient is to wear. The WMS system further includes additional components that are coupled to the harness, vest, or other garment. Alternately, these additional components may be adhered to the patient's skin by adhesive. These additional components include a unit that has a defibrillator, and sensing and therapy electrodes. When the patient wears this WMS, the sensing electrodes may make good electrical contact with the patient's skin and therefore can help sense the patient's Electrocardiogram ("ECG"). If the unit detects a shockable heart arrhythmia from the ECG, then the unit delivers an appropriate electric shock to the patient's body through the therapy electrodes. The shock can pass through the patient's heart and may restore its normal rhythm, thus saving their life.

All subject matter discussed in this Background section of this document is not necessarily prior art, and may not be presumed to be prior art simply because it is presented in this Background section. Additionally, any reference to any prior art in this description is not, and should not be taken as, an acknowledgement or any form of suggestion that such prior art forms parts of the common general knowledge in any art in any country. Along these lines, any recognition of problems in the prior art discussed in this Background section or associated with such subject matter should not be treated as prior art, unless expressly stated to be prior art. Rather, the discussion of any subject matter in this Background section should be treated as part of the approach taken towards the particular problem by the inventors. This approach in and of itself may also be inventive.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein like reference numerals refer to like parts throughout the various views unless otherwise specified:

FIG. 8 is a schematic diagram illustrating an exemplary high side gate drive circuit, according to one embodiment.

FIG. 9 is a diagram of a controller that may be implemented in the processor block of FIG. 6, according to one embodiment.

FIG. 14 is a table implemented in software and use to vary the duty cycle of a digital output, according to one embodiment.

SUMMARY

Figure 1:
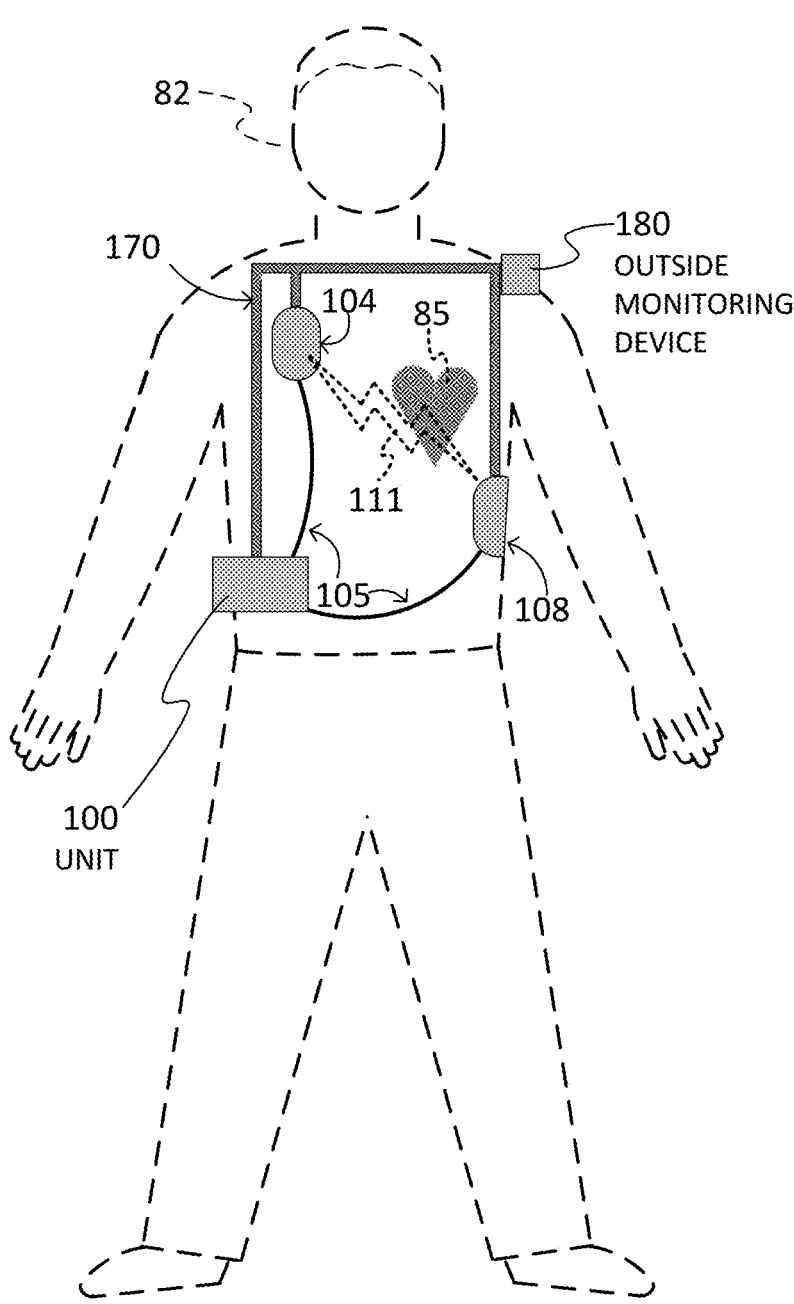
FIG. 1 is a diagram of sample components of a wearable medical system ("WMS") that implements a wearable cardioverter defibrillator ("WCD"), and which is made according to embodiments.

The present description gives instances of apparatus and methods for generating pacing pulses in a wearable cardioverter defibrillator. In one aspect the WCD circuitry includes a power source such as a battery coupled to a charger that provides charge energy to an energy storage module. Control circuitry is operatively coupled to the charger, the energy storage module, and the output circuitry, and configured to cause the WCD circuitry to generate pacing pulses delivered to one or more therapy electrodes (attached to an ambulatory patient) without a current source. The WCD circuitry includes one or more processing elements that are used to execute instructions provided by one or more software modules that are configured to support various functionality, including controlling generation of pacing pulses.

In embodiments, the WCD circuitry may be configured to generate and deliver pacing pulses to ambulatory patients using several approaches. For example, in some embodiments the charger and associated charge circuit is operated in a manner that emulates a current source. The WCD circuitry may generate pacing pulses without impedance feedback in some embodiments, while other embodiments may employ various feedback schemes that utilize impedance measurement and/or detected waveform parameters. An advantage and/or benefit of embodiments the implement a charger to emulate a current source is this enables a WCD to perform at a similar level to conventional WCDs that employ current sources without the added cost of a current source.

According to other aspects, controlling of the charger and associated circuitry is implemented by software executing on one or more processing elements, such as a controller or embedded processor. The software may be upgradable to provide enhanced functionality. The software also provides a user interface to enable various functionality to be enabled or disabled and for various modes and associated parameters to be set.

These and other features and advantages of the claimed invention will become more readily apparent in view of the embodiments described and illustrated in this specification, namely in this written specification and the associated drawings.

DETAILED DESCRIPTION

Embodiments of apparatus and methods for WCD pacing pulse generation are described herein. In the following description, numerous specific details are set forth to provide a thorough understanding of embodiments of the invention. One skilled in the relevant art will recognize, however, that the invention can be practiced without one or more of the specific details, or with other methods, components, materials, etc. In other instances, well-known structures, materials, or operations are not shown or described in detail to avoid obscuring aspects of the invention.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

For clarity, individual components in the Figures herein may also be referred to by their labels in the Figures, rather than by a particular reference number. Additionally, reference numbers referring to a particular type of component (as opposed to a particular component) may be shown with a reference number followed by "(typ)" meaning "typical." It will be understood that the configuration of these components will be typical of similar components that may exist but are not shown in the drawing Figures for simplicity and clarity or otherwise similar components that are not labeled with separate reference numbers. Conversely, "(typ)" is not to be construed as meaning the component, element, etc. is typically used for its disclosed function, implement, purpose, etc.

A wearable medical system ("WMS") that implements a wearable cardioverter defibrillator ("WCD") according to embodiments may protect an ambulatory patient by electrically restarting their heart if needed. Such a WMS may have a number of components. These components can be provided separately as modules that can be interconnected, or can be combined with other components, and so on. Examples are now described.

FIG. 1 depicts a patient 82. The patient 82 may also be referred to as the person 82 and/or wearer 82, since the patient 82 is wearing components of the WMS. The patient 82 is ambulatory, which means that, while wearing the wearable component(s) of the WMS, the patient 82 can walk around, be in a vehicle, and so on. In other words, the patient 82 is not necessarily bed-ridden. While the patient 82 may be considered to be also a "user" of the WMS, this definition is not exclusive to the patient 82. For instance, a user of the WMS may also be a clinician such as a doctor, nurse, emergency medical technician (EMT), or other similarly tasked and/or empowered individual or group of individuals. In some cases, a user may even be a bystander. The particular context of these and other related terms within this description should be interpreted accordingly.

A WMS that implements a WCD according to embodiments can be configured to defibrillate the patient who is wearing the designated components of the WMS. Defibrillating can be by the WMS delivering an electrical charge to the patient's body in the form of an electric shock. The electric shock can be delivered in one or more pulses.

In particular, FIG. 1 also depicts components of a WMS that implements a WCD and is made according to embodiments. One such component is a support structure 170 that is wearable by the ambulatory patient 82. Accordingly, the support structure 170 can be configured to be worn by the ambulatory patient 82 for at least several hours per day, and also during the night. That, for at least several days, and maybe even a few months. It will be understood that the support structure 170 is shown only generically in FIG. 1, and in fact partly conceptually. FIG. 1 is provided merely to illustrate concepts about the support structure 170, and is not to be construed as limiting how the support structure 170 is implemented, or how it is worn.

The support structure 170 can be implemented in many different ways. For example, it can be implemented in a single component or a combination of multiple components. In embodiments, the support structure 170 could include a vest, a half-vest, a garment, etc. In such embodiments such items can be worn similarly to analogous articles of clothing. In embodiments, the support structure 170 could include a harness, one or more belts or straps, etc. In such embodiments, such items can be worn by the patient around the torso, hips, over the shoulder, etc. In embodiments, the support structure 170 can include a container or housing, which can even be waterproof. In such embodiments, the support structure can be worn by being attached to the patient's body by adhesive material, for example as shown and described in U.S. Pat. No. 8,024,037. The support structure 170 can even be implemented as described for the support structure of US Published App. No. US2017/0056682, which is incorporated herein by reference. Of course, in such embodiments, the person skilled in the art will recognize that additional components of the WMS can be in the housing of a support structure instead of being attached externally to the support structure, for example as described in the US2017/0056682 document. There can be other examples.

The embodiments of FIG. 1 include a sample unit 100. In embodiments, the unit 100 is sometimes called a main electronics module. In embodiments, the unit 100 implements an external defibrillator. In embodiments, the unit 100 implements an external pacemaker instead of, or in addition to, an external defibrillator. In embodiments that include a pacemaker, the WMS may detect when the patient's heart rhythm slows down or when the patient has asystole, and the pacemaker may pace to increase the heart rate. Of course, if the patient does not respond to the pacing and their heart rhythm deteriorates further, the WMS may then later cause one or more defibrillation shocks to be delivered.

The embodiments of FIG. 1 also include sample therapy electrodes 104, 108, which are electrically coupled to unit 100 via electrode leads 105. The therapy electrodes 104, 108 are also called defibrillation electrodes or just electrodes. The therapy electrodes 104, 108 can be configured to be worn by the patient 82 in a number of ways. For instance, the unit 100 and the therapy electrodes 104, 108 can be coupled to the support structure 170, directly or indirectly. In other words, the support structure 170 can be configured to be worn by the ambulatory patient 82 so as to maintain at least one of the therapy electrodes 104, 108 on the body of the ambulatory patient 82, while the patient 82 is moving around, etc. The therapy electrodes 104, 108 can be thus maintained on the body by being attached to the skin of the patient 82, simply pressed against the skin directly or through garments, etc. In some embodiments the therapy electrodes 104, 108 are not necessarily pressed against the skin, but become biased that way upon sensing a condition that could merit intervention by the WMS. In addition, many of the components of the unit 100 can be considered coupled to the support structure 170 directly, or indirectly, via at least one of the therapy electrodes 104, 108.

When the therapy electrodes 104, 108 make good electrical contact with the body of the patient 82, the unit 100 can administer, via the therapy electrodes 104, 108, a brief, strong electric pulse 111 through the body. The pulse 111 is also known as defibrillation pulse, shock, defibrillation shock, therapy, electrotherapy, therapy shock, etc. The pulse 111 is intended to go through and restart the heart 85, in an effort to save the life of the patient 82. The defibrillation pulse 111 can have an energy suitable for its purpose, such as at least 100 Joule ("J"), 200 J, 300 J, and so on. For pacemaker embodiments, the pulse 111 could alternately be depicting a pacing pulse. At least some of the stored electrical charge can be caused to be discharged via at least two of the therapy electrodes 104, 108 through the ambulatory patient 82, so as to deliver to the ambulatory patient 82 a sequence of pacing pulses. The pacing pulses may be periodic, and thus define a pacing period and the pacing rate. There is no requirement, however, that the pacing pulses be exactly periodic. A pacing pulse can have an energy suitable for its purpose, such as at most 10 J, 5 J, usually about 2 J, and so on. The pacemaker therefore is delivering current to the heart to start a heartbeat. In either case, the pulse 111 has a waveform suitable for this purpose.

A prior art defibrillator typically decides whether to defibrillate or not based on an ECG signal of the patient. However, the unit 100 may initiate defibrillation, or hold-off defibrillation, based on a variety of inputs, with the ECG signal merely being one of these inputs.

A WMS that implements a WCD according to embodiments can collect data about one or more parameters of the patient 82. For collecting such data, the WMS may optionally include at least an outside monitoring device 180. The device 180 is called an "outside" device because it could be provided as a standalone device, for example not within the housing of the unit 100. The device 180 can be configured to sense or monitor at least one local parameter. A local parameter can be a parameter of the patient 82, or a parameter of the WMS, or a parameter of the environment, as described later in this document.

For some of these parameters, the device 180 may include one or more sensors or transducers. Each one of such sensors can be configured to sense a parameter of the patient 82, or of the environment, and to render an input responsive to the sensed parameter. In some embodiments the input is quantitative, such as values of a sensed parameter; in other embodiments the input is qualitative, such as informing whether or not a threshold is crossed, and so on. Such inputs about the patient 82 are also called physiological inputs and patient inputs. In embodiments, a sensor can be construed more broadly, as encompassing more than one individual sensors.

Optionally, the device 180 is physically coupled to the support structure 170. In addition, the device 180 may be communicatively coupled with other components that are coupled to the support structure 170, such as with the unit 100. Such communication can be implemented by the device 180 itself having a communication module, as will be deemed applicable by a person skilled in the art in view of this description.

A WMS that implements a WCD according to embodiments preferably includes sensing electrodes, which can sense an ECG of the patient. In embodiments, the device 180 stands for such sensing electrodes. In those embodiments, the sensed parameter of the patient 82 is the ECG of the patient, the rendered input can be time values of a waveform of the ECG signal, and so on.

In embodiments, one or more of the components of the shown WMS may be customized for the patient 82. This customization may include a number of aspects. For instance, the support structure 170 can be fitted to the body of the patient 82. For another instance, baseline physiological parameters of the patient 82 can be measured for various scenarios, such as when the patient is lying down (various orientations), sitting, standing, walking, running, and so on. These baseline physiological parameters can be the heart rate of the patient 82, motion detector outputs, one for each scenario, etc. The measured values of such baseline physiological parameters can be used to customize the WMS, in order to make its diagnoses more accurate, since patients' bodies differ from one another. Of course, such parameter values can be stored in a memory of the WMS, and so on. Moreover, a programming interface can be made according to embodiments, which receives such measured values of baseline physiological parameters.

The support structure 170 is configured to be worn by the ambulatory patient 82 so as to maintain the therapy electrodes 104, 108 on a body of the patient 82. As mentioned before, the support structure 170 can be advantageously implemented by clothing or one or more garments. Such clothing or garments do not have the function of covering a person's body as a regular clothing or garments do, but the terms "clothing" and "garment" are used in this art for certain components of the WMS intended to be worn on the human body in the same way as clothing and garments are. In fact, such clothing and garments of a WMS can be of different sizes for different patients, and even be custom-fitted around the human body. And, regular clothing can often be worn over portions or all of the support structure 170. Examples of the support structure 170 are now described.

Figure 2A:
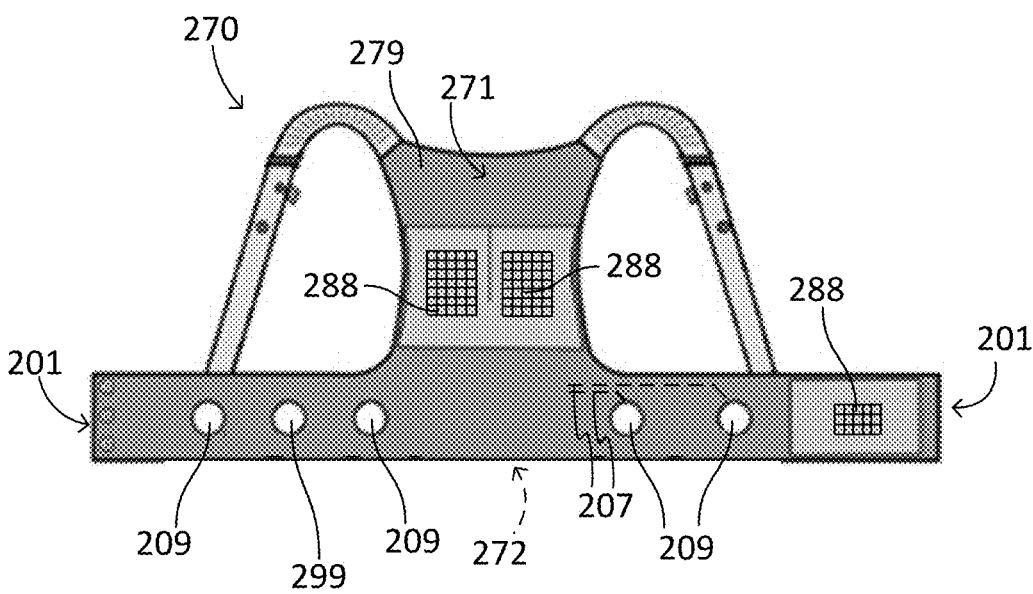
FIG. 2A is a diagram showing a view of the inside of a sample garment embodiment that can be a support structure of a WMS that implements a WCD, such as that of FIG. 1.

FIG. 2A shows a support structure 270 of a WMS that implements a WCD, such as the support structure 170 of FIG. 1. The support structure 270 is implemented by a vest-like wearable garment 279 that is shown flat, as if placed on a table. The inside side 271 of the garment 279 is seen as one looks at the diagram from the top, and it is the side contacting the body of the wearer when the garment 279 is worn. The outside side 272 of the garment 279 is opposite the inside side 271. To be worn, tips 201 can be brought together while surrounding the torso, and affixed to each other, either at their edges or partly overlapping. Appropriate mechanisms can hold together the tips 201, such as buttons/snaps, hooks and loops, Velcro® material, and so on.

The garment 279 can be made of suitable combinations of materials, such as fabric, linen, plastic, and so on. In places, the garment 279 can have two adjacent surfaces for defining between them pockets for the pads of the electrodes, for enclosing the leads or wires of the electrodes, and so on. Moreover, in FIG. 2A one can see meshes 288 which are the interior side of pockets accessible from the outside. The meshes can be made from flexible material such as loose netting, and so on.

ECG signals in a WMS that implements a WCD may sometimes include too much electrical noise for analyzing the ECG signal. To ameliorate the problem, multiple ECG sensing electrodes are provided in embodiments. These multiple ECG sensing electrodes define different vectors for sensing ECG signals along different ECG channels. These different ECG channels therefore present alternative options for analyzing the patient's ECG signal. The patient impedance along each ECG channel may also be sensed, and thus be part of the patient input.

In the example of FIG. 2A, multiple ECG sensing electrodes 209 are provided, which can be seen protruding from the inside surface of the garment 279. These ECG sensing electrodes 209 can be affixed to the inside surface of the garment 279, while their leads or wires 207 can be located mostly or completely within the garment 279. These ECG sensing electrodes 209 are intended to contact the skin of the person when the garment 279 is worn, and can be made from suitable material for good electrical contact. Such a material can be a metal, such as silver, or other sufficiently conductive materials. An additional ECG-sensing electrode 299 may play the role of a Right Leg Drive ("RLD") in the ECG analysis. In this context "RLD" is a custom electrical term, and embodiments do not require that the electrode 299 be actually placed on a leg of the patient.

Figure 2B:
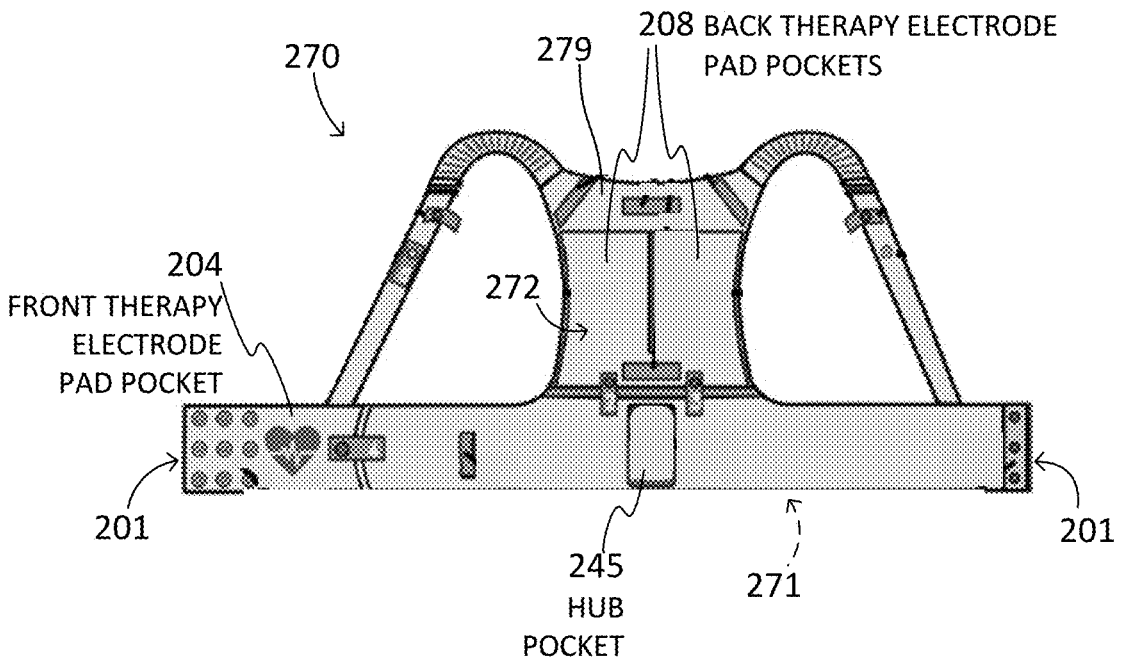
FIG. 2B is a diagram showing a view of the outside of the sample garment of FIG. 2A.

FIG. 2B shows the outside side 272 of the garment 279. One can appreciate that pockets are included that are accessible from the outside, such as a hub pocket 245. In addition, a pocket 204 is provided for a front therapy electrode pad, plus two pockets 208 are provided for two back therapy electrode pads. The pads of the therapy electrodes can be placed in the pockets 204, 208, and contact the skin of the patient through the respective meshes 288 that were seen in FIG. 2A. The electrical contact can be facilitated by conductive fluid that can be deployed in the area, when the time comes for a shock.

Figure 2C:
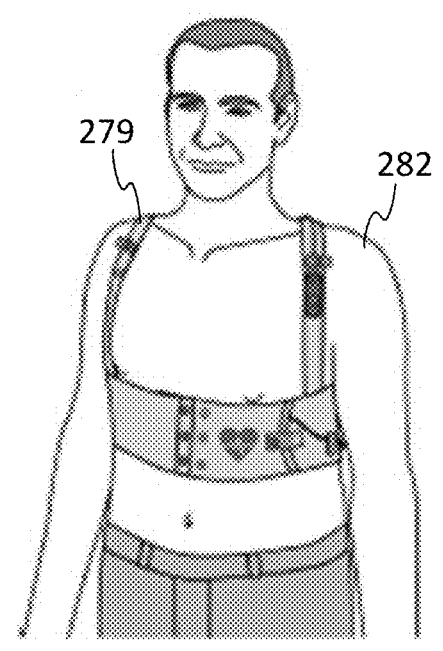
FIG. 2C is a diagram showing a front view of how the sample garment of FIGS. 2A and 2B is intended to be worn by a patient.

FIG. 2C is a diagram showing a front view of how the garment 279 would be worn by a patient 282. It will be appreciated that the previously described ECG sensing electrodes 209, 299 of FIG. 2A are maintained against the body of the patient 282 from the inside side of the garment 279, and thus are not visible in FIG. 2C.

Figure 2D:
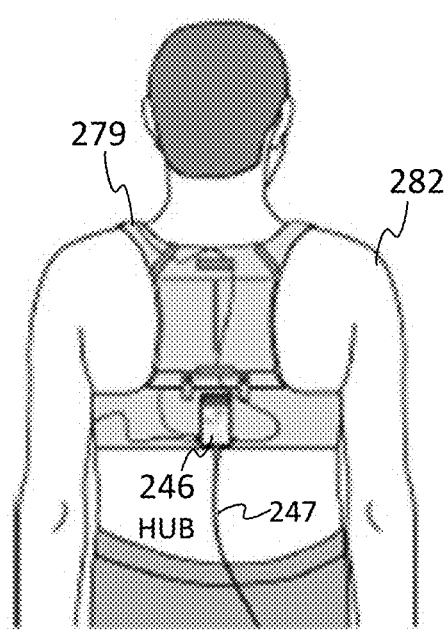
FIG. 2D is a diagram showing a back view of how the sample garment of FIGS. 2A and 2B is intended to be worn by a patient.

FIG. 2D is a diagram showing the back view of FIG. 2C. A hub 246 has been placed in the hub pocket 245 that is shown in FIG. 2B. A cable 247 emerges from the hub 246, which can be coupled with a unit for the system, as described later in this document.

FIGS. 2A-2D do not show any physical support for a unit such as the unit 100 of FIG. 1. In these embodiments, such a unit may be carried in a purse, on a belt, by a strap over the shoulder, or additionally by further adapting the garment 279, and so on.

Figure 3:
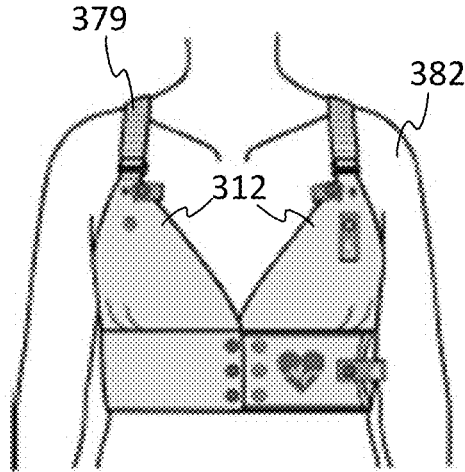
FIG. 3 is a diagram showing a partial front view of another patient wearing a sample garment embodiment of an alternate style as worn by a patient, and which can be a support structure of a WMS that implements a WCD such as that of FIG. 1.

FIG. 3 is a diagram showing a partial front view of another patient 382 wearing another garment 379. The garment 379 is of an alternate style than the garment 279, in that it further includes breast support receptacles 312, as was described for instance in U.S. Pat. No. 10,926,080. This style of garment may be more comfortable if the patient 382 is a woman.

Figure 4:
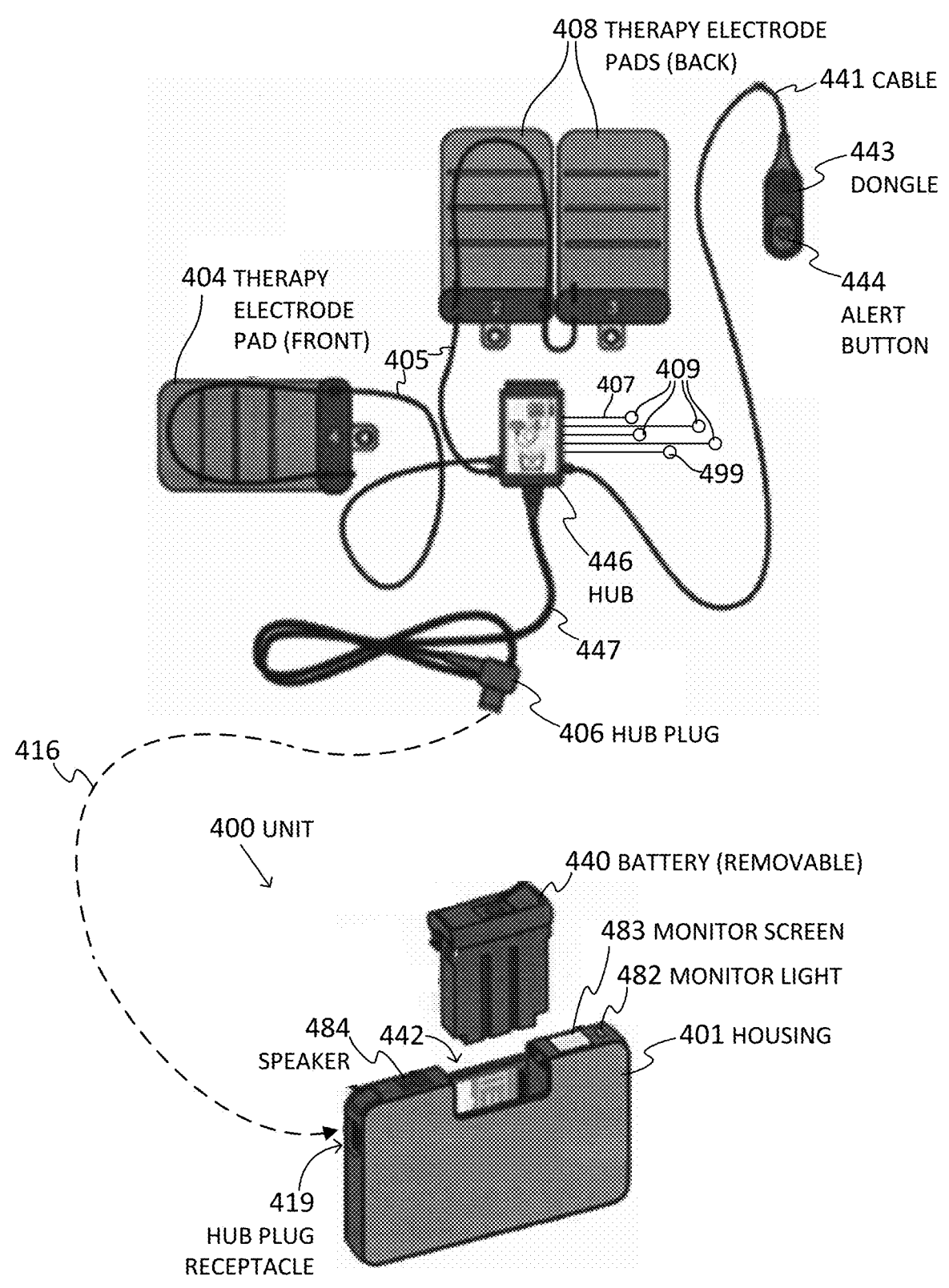
FIG. 4 is a diagram showing sample embodiments of electronic components of a WMS that implements a WCD, and which can be used with the garment of FIG. 2A or of FIG. 3.

FIG. 4 shows sample electronic components that can be used with the garments 279, 379. The components of FIG. 4 include a unit 400, shown at the lower portion of FIG. 4. The unit 400 includes a housing 401, and a hub plug receptacle 419 at the housing 401.

The unit 400 includes a battery opening 442 at the housing 401. The battery opening 442 is configured to receive a removable battery 440. A system according to embodiments can have two identical such batteries 440, one plugged into the housing 401 while another one (not shown) is being charged by a charger (not shown). The batteries can then be interchanged when needed.

The unit 400 also includes devices for implementing a user interface. In this example, these devices include a monitor light 482, a monitor screen 483 and a speaker 484. Additional devices may include a vibrating mechanism, and so on.

The unit 400 can implement many of the functions of the unit 100 of FIG. 1. In the embodiment of FIG. 4, however, some of the functions of the unit 100 are implemented instead by a separate hub 446, which can be connected to the unit 400. The hub 446 is smaller and lighter than the unit 400, and can accommodate multiple electrical connections to other components of FIG. 4. A cable 447, similar to the cable 247 of FIG. 2D, emerges from the hub 446 and terminates in a hub plug 406. The hub plug 406 can be plugged into the hub plug receptacle 419 of the unit 400 according to an arrow 416.

ECG sensing electrodes 409, 499, plus their wires or leads 407 are further shown conceptually in FIG. 4 for complete-ness. The wires or leads 407 that can be configured to be coupled to the hub 446.

The components of FIG. 4 also include the therapy electrode pads 404, 408. The therapy electrode pad 404 can be inserted into the pocket 204 of FIG. 2B, while the therapy electrode pads 408 can be inserted into the pockets 208 of FIG. 2B. The shock is generated between the therapy electrode pad 404 and the therapy electrode pads 408 taken together. Indeed, the therapy electrode pads 408 are electri-cally connected to each other. The therapy electrode pads 404, 408, have leads 405, which can be configured to be coupled to the hub 446.

The components of FIG. 4 further include a dongle 443 with an alert button 444. The dongle 443 can be configured to be coupled to the hub 446 via a cable 441. The alert button 444 can be used by the patient to give emergency input to the WMS. For instance, the alert button 444 can be used by the patient to notify the system that the patient is actually alive and an imminent shock is not actually needed, which may otherwise happen in the event of a false positive detection of a shockable heart rhythm of the patient.

Figure 5:
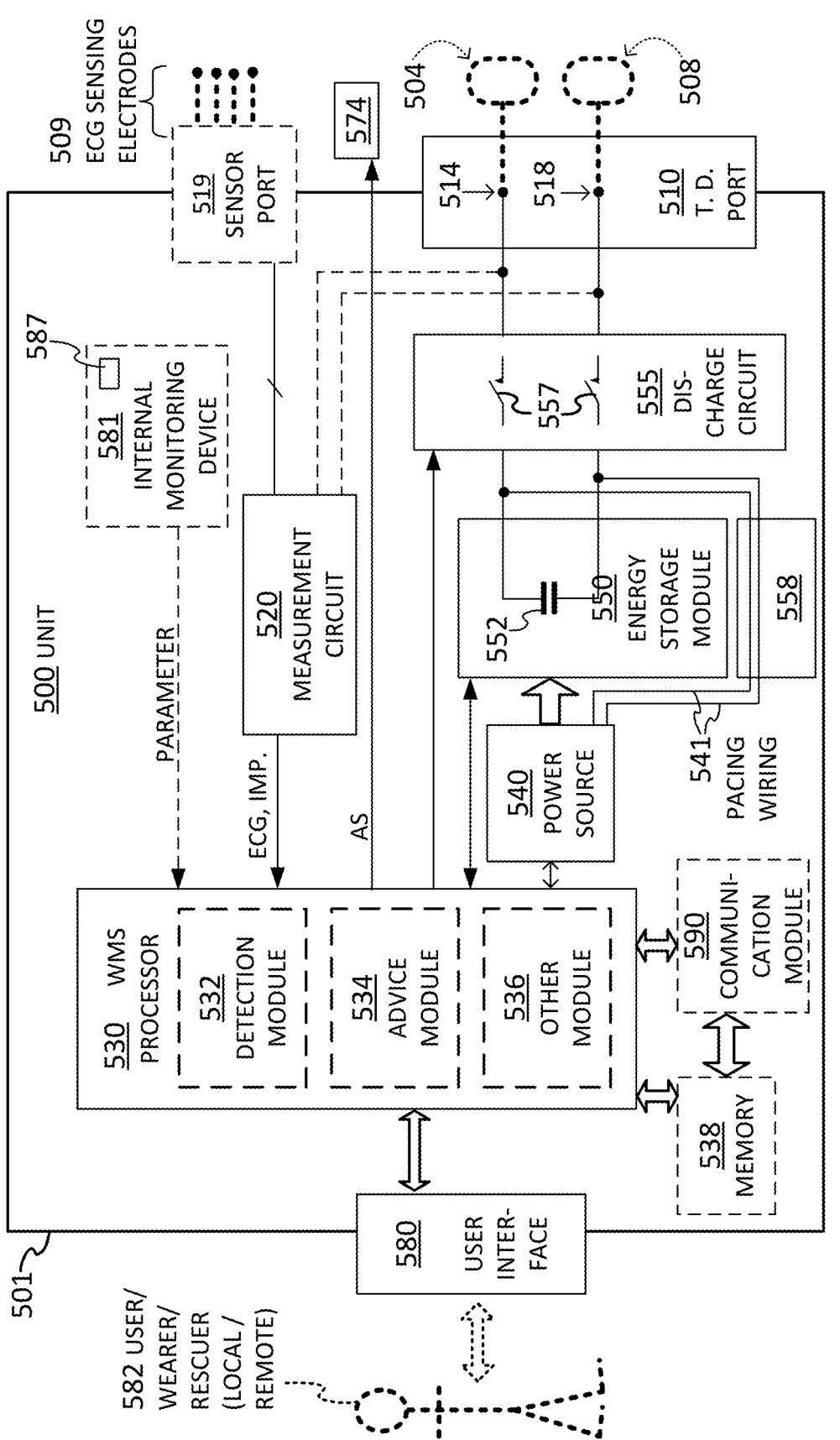
FIG. 5 is a diagram showing sample components of a unit of FIG. 1, which is made according to embodiments.

FIG. 5 shows a sample unit 500, which could be the unit 100 of FIG. 1. The unit 500 implements an external defi-brillator and/or a pacemaker. The sample unit 500 thus combines the functions of the unit 400 and of the hub 446 of FIG. 4. The components shown in FIG. 5 can be provided in a housing 501, which may also be referred to as casing 501.

The unit 500 may include a user interface (UI) 580 for a user 582. User 582 can be the patient 82, also known as patient 582, also known as the wearer 582. Or, the user 582 can be a local rescuer at the scene, such as a bystander who might offer assistance, or a trained person. Or, the user 582 might be a remotely located trained caregiver in communi-cation with the WMS, such as a clinician.

The user interface 580 can be made in a number of ways. The user interface 580 may include output devices, which can be visual, audible or tactile, for communicating to a user by outputting images, sounds or vibrations. Images, sounds, vibrations, and anything that can be perceived by user 582 can also be called human-perceptible indications. As such, an output device according to embodiments can be config-ured to output a human-perceptible indication (HPI). Such HPIs can be used to alert the patient, sound alarms that may be intended also for bystanders, and so on. There are many instances of output devices. For example, an output device can be a light that can be turned on and off, a screen to display what is sensed, detected and/or measured, and provide visual feedback to the local rescuer 582 for their resuscitation attempts, and so on. Another output device can be a speaker, which can be configured to issue voice prompts, alerts, beeps, loud alarm sounds and/or words, and so on. These can also be for bystanders, when defibrillating or just pacing, and so on. Examples of output devices were the monitor light 482, the monitor screen 483 and the speaker 484 of the unit 400 seen in FIG. 4.

The user interface 580 may further include input devices for receiving inputs from users. Such users can be the patient 82, 582, perhaps a local trained caregiver or a bystander, and so on. Such input devices may include various controls, such as pushbuttons, keyboards, touchscreens, one or more microphones, and so on. An input device can be a cancel switch, which is sometimes called an "I am alive" switch or "live man" switch. In some embodiments, actuating the cancel switch can prevent the impending delivery of a shock, or of pacing pulses. In particular, in some embodiments a speaker of the WMS is configured to output a warning prompt prior to an impending or planned defibrillation shock or a sequence of pacing pulses being caused to be delivered, and the cancel switch is configured to be actuated by the ambulatory patient 82 in response to the warning prompt being output. In such embodiments, the impending or planned defibrillation shock or sequence of the pacing pulses is not caused to be delivered. An example of a cancel switch was the alert button 444 seen in FIG. 4.

The unit 500 may include an internal monitoring device 581. The device 581 is called an "internal" device because it is incorporated within the housing 501. The monitoring device 581 can sense or monitor patient parameters such as patient physiological parameters, system parameters and/or environmental parameters, all of which can be called patient data. In other words, the internal monitoring device 581 can be complementary of, or an alternative to, the outside monitoring device 180 of FIG. 1. Allocating which of the parameters are to be monitored by which of the monitoring devices 180, 581 can be done according to design consid-erations. The device 581 may include one or more sensors, as also described elsewhere in this document.

Patient parameters may include patient physiological parameters. Patient physiological parameters may include, for example and without limitation, those physiological parameters that can be of any help in detecting by the WMS whether or not the patient is in need of a shock or other intervention or assistance. Patient physiological parameters may also optionally include the patient's medical history, event history and so on. Examples of such parameters include the above-described electrodes to detect the ECG, blood oxygen level, blood flow, blood pressure, blood per-fusion, pulsatile change in light transmission or reflection properties of perfused tissue, heart sounds, heart wall motion, breathing sounds and pulse. Accordingly, the monitoring devices 180, 581 may include one or more sensors or transducers configured to acquire patient physiological signals. Examples of such sensors and transducers include one or more electrodes to detect ECG data, a perfusion sensor, a pulse oximeter, a device for detecting blood flow (e.g. a Doppler device), a sensor for detecting blood pressure (e.g. a cuff), an optical sensor, illumination detectors and sensors perhaps working together with light sources for detecting color change in tissue, a motion sensor, a device that can detect heart wall movement, a sound sensor, a device with a microphone, an SpO2 sensor, and so on. In view of this disclosure, it will be appreciated that such sensors can help detect the patient's pulse, and can therefore also be called pulse detection sensors, pulse sensors, and pulse rate sensors. In addition, a person skilled in the art may implement other ways of performing pulse detection.

In some embodiments, the local parameter reflects a trend that can be detected in a monitored physiological parameter of the patient 82, 582. Such a trend can be detected by comparing values of parameters at different times over short and long terms. Parameters whose detected trends can particularly help a cardiac rehabilitation program include: a) cardiac function (e.g. ejection fraction, stroke volume, cardiac output, etc.); b) heart rate variability at rest or during exercise; c) heart rate profile during exercise and measurement of activity vigor, such as from the profile of an accelerometer signal and informed from adaptive rate pacemaker technology; d) heart rate trending; e) perfusion, such as from SpO2, CO2, or other parameters such as those mentioned above, f) respiratory function, respiratory rate, etc.; g) motion, level of activity; and so on. Once a trend is detected, it can be stored and/or reported via a communication link, along perhaps with a warning if warranted. From the report, a physician monitoring the progress of the patient 82, 582 will know about a condition that is either not improving or deteriorating.

Patient state parameters include recorded aspects of the patient 582, such as motion, posture, whether they have spoken recently plus maybe also what they said, and so on, plus optionally the history of these parameters. Or, one of these monitoring devices could include a location sensor such as a Global Positioning System (GPS) location sensor. Such a sensor can detect the location, plus a speed of patient can be detected as a rate of change of location over time. Many motion detectors output a motion signal that is indicative of the motion of the detector, and thus of the patient's body. Patient state parameters can be very helpful in narrowing down the determination of whether SCA is indeed taking place.

A WMS made according to embodiments may thus include a motion detector. In embodiments, a motion detector can be implemented within the outside monitoring device 180 or within the internal monitoring device 581. A motion detector of a WMS according to embodiments can be configured to detect a motion event. A motion event can be defined as is convenient, for example a change in posture or motion from a baseline posture or motion, etc. In such cases, a sensed patient parameter is motion. Such a motion detector can be made in many ways as is known in the art, for example by using an accelerometer and so on. In this example, a motion detector 587 is implemented within the monitoring device 581.

System parameters of a WMS can include system identification, battery status, system date and time, reports of self-testing, records of data entered, records of episodes and intervention, and so on. In response to the detected motion event, the motion detector may render or generate, from the detected motion event or motion, a motion detection input that can be received by a subsequent device or functionality.

Environmental parameters can include ambient temperature and pressure. Moreover, a humidity sensor may provide information as to whether or not it is likely raining. Presumed patient location could also be considered an environmental parameter. The patient location could be presumed, if the monitoring device 180 or 581 includes a GPS location sensor as per the above, and if it is presumed or sensed that the patient is wearing the WMS.

The unit 500 includes a therapy delivery port 510 and a sensor port 519 in the housing 501. In contrast, in FIG. 4 these ports are located at the hub 446.

In FIG. 5, the therapy delivery port 510 can be a socket in the housing 501, or other equivalent structure. The therapy delivery port 510 includes electrical nodes 514, 518. Therapy electrodes 504, 508 are shown, which can be as the therapy electrodes 104, 108. Leads of the therapy electrodes 504, 508, such as the leads 105 of FIG. 1, can be plugged into the therapy delivery port 510, so as to make electrical contact with the nodes 514, 518, respectively. It is also possible that the therapy electrodes 504, 508 are connected continuously to the therapy delivery port 510, instead. Either way, the therapy delivery port 510 can be used for guiding, via electrodes, to the wearer at least some of the electrical charge that has been stored in an energy storage module 550 that is described more fully later in this document. When thus guided, the electric charge will cause the shock 111 to be delivered.

The sensor port 519 is also in the housing 501, and is also sometimes known as an ECG port. The sensor port 519 can be adapted for plugging in the leads of ECG sensing electrodes 509. The ECG sensing electrodes 509 can be as the ECG sensing electrodes 209. The ECG sensing electrodes 509 in this example are distinct from the therapy electrodes 504, 508. It is also possible that the sensing electrodes 509 can be connected continuously to the sensor port 519, instead. The electrodes 509 can be types of transducers that can help sense an ECG signal of the patient, e.g., a 12-lead signal, or a signal from a different number of leads, especially if they make good electrical contact with the body of the patient and in particular with the skin of the patient. As with the therapy electrodes 504, 508, the support structure can be configured to be worn by the patient 582 so as to maintain the sensing electrodes 509 on a body of the patient 582. For example, the sensing electrodes 509 can be attached to the inside of the support structure 170 for making good electrical contact with the patient, similarly with the therapy electrodes 504, 508.

Optionally a WMS according to embodiments also includes a fluid that it can deploy automatically between the electrodes and the patient's skin. The fluid can be conductive, such as by including an electrolyte, for establishing a better electrical contact between the electrodes and the skin. Electrically speaking, when the fluid is deployed, the electrical impedance between each electrode and the skin is reduced. Mechanically speaking, the fluid may be in the form of a low-viscosity gel. As such, it will not flow too far away from the location it is released. The fluid can be used for both the therapy electrodes 504, 508, and for the sensing electrodes 509.

The fluid may be initially stored in a fluid reservoir, not shown in FIG. 5. Such a fluid reservoir can be coupled to the support structure. In addition, a WMS according to embodiments further includes a fluid deploying mechanism 574. The fluid deploying mechanism 574 can be configured to cause at least some of the fluid to be released from the reservoir, and be deployed near one or both of the patient body locations to which the therapy electrodes 504, 508 are configured to be attached to the patient's body. In some embodiments, the fluid deploying mechanism 574 is activated prior to the electrical discharge responsive to receiving an activation signal AS from the processor 530, which is described more fully later in this document.

In some embodiments, unit 500 also includes a measurement circuit 520, as one or more of its modules working together with its sensors and/or transducers. The measurement circuit 520 senses one or more electrical physiological signals of the patient from sensor port 519, if provided. Even if the unit 500 lacks a sensor port, the measurement circuit 520 may optionally obtain physiological signals through the nodes 514, 518 instead, when the therapy electrodes 504, 508 are attached to the patient. In these cases, the input reflects an ECG measurement. The patient parameter can be an ECG, which can be sensed as a voltage difference between electrodes 504, 508. In addition, the patient parameter can be an impedance (IMP. or Z), which can be sensed between the electrodes 504, 508 and/or between the connections of the sensor port 519 considered pairwise as channels. Sensing the impedance can be useful for detecting, among other things, whether these electrodes 504, 508 and/or the sensing electrodes 509 are not making good electrical contact with the patient's body at the time. These patient physiological signals may be sensed when available. The measurement circuit 520 can then render or generate information about them as inputs, data, other signals, etc. As such, the measurement circuit 520 can be configured to render a patient input responsive to a patient parameter sensed by a sensor. In some embodiments, the measurement circuit 520 can be configured to render a patient input, such as values of an ECG signal, responsive to the ECG signal sensed by the ECG sensing electrodes 509. More strictly speaking, the information rendered by the measurement circuit 520 is output from it, but this information can be called an input because it is received as an input by a subsequent stage, device or functionality.

Unit 500 also includes a processor 530. The processor 530 may be implemented in a number of ways. Such ways include, by way of example and not of limitation, digital and/or analog processors such as microprocessors and Digital Signal Processors (DSPs), controllers such as microcontrollers, software running in a machine, programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

The processor 530 may include, or have access to, a non-transitory storage medium, such as a memory 538 that is described more fully later in this document. Such a memory can have a non-volatile component for storage of machine-readable and machine-executable instructions. A set of such instructions can also be called a program. The instructions, which may also be referred to as "software," generally provide functionality by performing acts, operations and/or methods as may be disclosed herein or understood by one skilled in the art in view of the disclosed embodiments. In some embodiments, and as a matter of convention used herein, instances of the software may be referred to as a "module" and by other similar terms. Generally, a module includes a set of the instructions so as to offer or fulfill a particular functionality. Embodiments of modules and the functionality delivered are not limited by the embodiments described in this document.

The processor 530 can be considered to have a number of modules. One such module can be a detection module 532. The detection module 532 can include a Ventricular Fibrillation (VF) detector. The patient's sensed ECG from measurement circuit 520, which can be available as inputs, data that reflect values, or values of other signals, may be used by the VF detector to determine whether the patient is experiencing VF. Detecting VF is useful, because VF typically results in SCA. The detection module 532 can also include a Ventricular Tachycardia (VT) detector for detecting VT, and so on.

Another such module in processor 530 can be an advice module 534, which generates advice for what to do. The advice can be based on outputs of the detection module 532. There can be many types of advice according to embodiments. In some embodiments, the advice is a shock/no shock determination that processor 530 can make, for example via advice module 534. The shock/no shock determination can be made by executing a stored Shock Advisory Algorithm. A Shock Advisory Algorithm can make a shock/no shock determination from one or more ECG signals that are sensed according to embodiments, and determine whether or not a shock criterion is met. The determination can be made from a rhythm analysis of the sensed ECG signal or otherwise. For example, there can be shock decisions for VF, VT, etc.

In perfect conditions, a very reliable shock/no shock determination can be made from a segment of the sensed ECG signal of the patient. In practice, however, the ECG signal is often corrupted by electrical noise, which makes it difficult to analyze. Too much noise sometimes causes an incorrect detection of a heart arrhythmia, resulting in a false alarm to the patient. Noisy ECG signals may be handled as described in U.S. Pat. No. 10,918,879 ("Wearable cardioverter defibrillator (WCD) system reacting to high-amplitude ECG noise") and U.S. Pat. No. 11,103,717 ("Wearable cardioverter defibrillator (WCD) system reacting to high-frequency ECG noise"), which are incorporated herein by reference for all purposes.

The processor 530 can include additional modules, such as other module 536, for other functions. In addition, if the internal monitoring device 581 is indeed provided, the processor 530 may receive its inputs, etc.

The unit 500 optionally further includes a memory 538, which can work together with the processor 530. The memory 538 may be implemented in a number of ways. Such ways include, by way of example and not of limitation, volatile memories, Nonvolatile Memories (NVM), Read-Only Memories (ROM), Random Access Memories (RAM), magnetic disk storage media, optical storage media, smart cards, flash memory devices, any combination of these, and so on. The memory 538 is thus a non-transitory storage medium. The memory 538, if provided, can include programs for the processor 530, which the processor 530 may be able to read and execute. More particularly, the programs can include sets of instructions in the form of code, which the processor 530 may be able to execute upon reading. Executing is performed by physical manipulations of physical quantities, and may result in functions, operations, processes, acts, actions and/or methods to be performed, and/or the processor 530 to cause other devices or components or blocks to perform such functions, operations, processes, acts, actions and/or methods. The programs can be operational for the inherent needs of the processor 530, and can also include protocols and ways that decisions can be made by the advice module 534. In addition, the memory 538 can store prompts for the user 582, if this user is a local rescuer. Moreover, the memory 538 can store data. This data can include patient data, system data and environmental data, for example as learned by the internal monitoring device 581 and the outside monitoring device 180. The data can be stored in the memory 538 before it is transmitted out of the unit 500, or be stored there after it is received by the unit 500.

The unit 500 can optionally include a communication module 590, for establishing one or more wired or wireless communication links with other devices of other entities, such as a remote assistance center, Emergency Medical Services (EMS), and so on. The communication links can be used to transfer data and commands. The data may be patient data, event information, therapy attempted, CPR perfor- mance, system data, environmental data, and so on. For example, the communication module 590 may transmit wirelessly, e.g. on a daily basis, heart rate, respiratory rate, and other vital signs data to a server accessible over the internet, for instance as described in US App. Pub. No. 20140043149. This data can be analyzed directly by the patient's physician and can also be analyzed automatically by algorithms designed to detect a developing illness and then notify medical personnel via text, email, phone, etc. The module 590 may also include such interconnected sub-components as may be deemed necessary by a person skilled in the art, for example an antenna, portions of a processor, supporting electronics, outlet for a telephone or a network cable, etc.

The unit 500 may also include a power source 540, which is configured to provide electrical charge in the form of a current. To enable portability of the unit 500, the power source 540 typically includes a battery. Such a battery is typically implemented as a battery pack, which can be rechargeable or not. Sometimes a combination is used of rechargeable and non-rechargeable battery packs. An example of a rechargeable battery 540 was a battery 440 of FIG. 4. Other embodiments of the power source 540 can include an AC power override, for where AC power will be available, an energy-storing capacitor, and so on. Appropri- ate components may be included to provide for charging or replacing the power source 540. In some embodiments, the power source 540 is controlled and/or monitored by the processor 530.

The unit 500 may additionally include an energy storage module 550. The energy storage module 550 can be coupled to receive the electrical charge provided by the power source 540. The energy storage module 550 can be configured to store the electrical charge received by the power source 540. As such, the energy storage module 550 is where some electrical energy can be stored temporarily in the form of an electrical charge, when preparing it for discharge to admin- ister a shock. In embodiments, the module 550 can be charged from the power source 540 to the desired amount of energy, for instance as controlled by the processor 530. In typical implementations, the module 550 includes a capaci- tor 552, which can be a single capacitor or a system of capacitors, and so on. In some embodiments, the energy storage module 550 includes a device that exhibits high power density, such as an ultracapacitor. As described above, the capacitor 552 can store the energy in the form of an electrical charge, for delivering to the patient. In some embodiments, the energy storage module 550 may include a dump circuit or other circuitry (not shown) that may be selectively operated to dump some of the energy stored in capacitor 552.

As mentioned above, the patient is typically shocked when the shock criterion is met. In particular, in some embodiments the processor 530 is configured to determine from the patient input whether or not a shock criterion is met, and cause, responsive to the shock criterion being met, at least some of the electrical charge stored in the module 550 to be discharged via the therapy electrodes 104, 108 through the ambulatory patient 82 while the support struc- ture is worn by the ambulatory patient 82 so as to deliver the shock 111 to the ambulatory patient 82. Delivering the electrical charge is also known as discharging and shocking the patient.

For causing the discharge, the unit 500 moreover includes a discharge circuit 555. When the decision is to shock, the processor 530 can be configured to control the discharge circuit 555 to discharge through the patient at least some of all of the electrical charge stored in the energy storage module 550, especially in a desired waveform. When the decision is to merely pace, i.e., to deliver pacing pulses, the processor 530 can be configured to cause control the dis- charge circuit 555 to discharge through the patient at least some of the electrical charge provided by the power source 540. Since pacing requires lesser charge and/or energy than a defibrillation shock, in some embodiments pacing wiring 541 is provided from the power source 540 to the discharge circuit 555. The pacing wiring 541 is shown as two wires that bypass the energy storage module 550, and only go through a current-supplying circuit 558. As such, the energy for the pacing is provided by the power source 540 either via the pacing wiring 541, or through the energy storage module 550. And, in some embodiments where only a pacemaker is provided, the energy storage module 550 may not be needed if enough pacing current can be provided from the power source 540. Either way, discharging can be to the nodes 514, 518, and from there to the therapy electrodes 504, 508, so as to cause a shock to be delivered to the patient. The circuit 555 can include one or more switches 557. The switches 557 can be made in a number of ways, such as by an H-bridge, and so on. In some embodiments, different ones of the switches 557 may be used for a discharge where a defibril- lation shock is caused to be delivered, than for a discharge where the much weaker pacing pulses are caused to be delivered. The circuit 555 could also be thus controlled via the processor 530, and/or the user interface 580.

The pacing capability can be implemented in a number of ways. ECG sensing may be done in the processor, as mentioned elsewhere in this document, or separately, for demand or synchronous pacing. In some embodiments, however, pacing can be asynchronous. Pacing can be soft- ware controlled, e.g., by managing the defibrillation path, or a separate pacing therapy circuit (not shown) could be included, which can receive the ECG sensing, via the circuit 520 or otherwise.

A time waveform of the discharge may be controlled by thus controlling discharge circuit 555. The amount of energy of the discharge can be controlled by how much energy storage module has been charged, and also by how long the discharge circuit 555 is controlled to remain open.

The unit 500 can optionally include other components.

Figure 6:
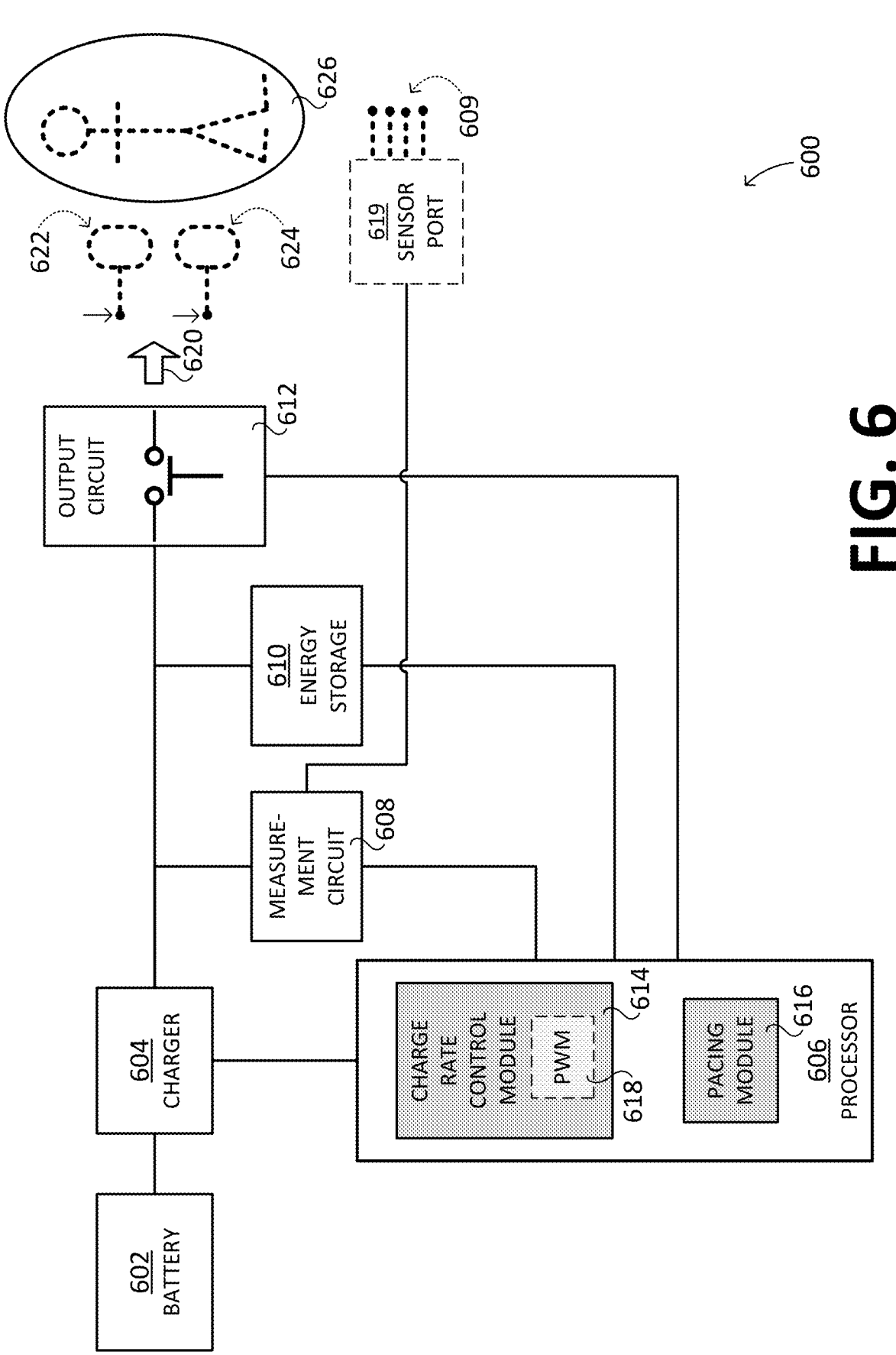
FIG. 6 is a top-level functional block diagram of a system for generating external "rescue" pacing pulses from a WCD without using a current source, according to one embodiment.

FIG. 6 shows a top-level functional block diagram of a system 600 of pertinent pacing hardware for generating external "rescue" pacing pulses from a WCD without using a current source as used in typical pacing hardware. Rescue pacing is a high current pacing to give the best opportunity for capture and keep the patient alive until the patient's intrinsic rhythm recovers or additional help arrives. In some embodiments, rescue pacing can keep the patient alive without necessarily bringing the patient back to consciousness.

System 600 includes a battery 602 that provides power to a charger 604, which is controlled by a processor 606. Additional components include a measurement circuit 608, an energy storage module 610, and an output circuit block 612. Processor 606 includes a charge rate control module 614 and a pacing module 616. The charge rate control module may include an optional pulse width modulation (PWM) module 618 in some embodiments. System 600 provides pacing pulses 620 to therapy electrodes 622 and 624, which are in contact with a patient 626. A sensor port 619 coupled to ECG sensing electrodes 609 is configured to send ECG signals generated by the ECG sensing electrodes to measurement circuit 608.

The functional blocks shown with a white background in FIG. 6 represent hardware that exists in some existing WCDs that do not currently provide pacing pulses. The functional blocks with a gray background (charge rate control module 614, pacing module 616 and optional PWM module 618) in processor 606 represent new modules to control the existing hardware to generate the pacing pulses in accordance with embodiments of the present disclosure. In some embodiments, the charge rate control function is implemented using both hardware (e.g., of the processor device) and the software of the charge rate control module.

In some embodiments, the pacing module is configured to enable processor 606 to detect arrhythmias that are to be treated with pacing pulses, and control when pacing pulses are to be delivered. For example, measurement circuit 608 (alone or in combination with processor 606 and/or other circuitry not shown in FIG. 6) may be configured to detect arrhythmias using the techniques disclosed in U.S. Patent Publication No. 2021/0052180 ("Cardiac monitoring system with supraventricular tachycardia (svt) classifications"), and U.S. Pat. No. 9,592,403 ("Wearable cardioverter defibrillator (WCD) system making shock/no shock determinations from multiple patient parameters"), U.S. Pat. No. 9,757,581 ("Wearable cardioverter defibrillator components making aggregate shock/no shock determination from two or more ECG signals), U.S. Pat. No. 11,058,885 ("Wearable cardioverter defibrillator (WCD) system detecting ventricular tachycardia and/or ventricular fibrillation using variable heart rate decision threshold"), U.S. Pat. No. 11,278,731 ("Wearable cardioverter defibrillator (WCD) system informing patient that it will not shock responsive to just-self-terminated cardiac arrhythmia"), and U.S. Pat. No. 11,471, 693 ("Wearable cardioverter defibrillator (WCD) system choosing to consider ECG signals from different channels per QRS complex widths of the ECG signals"), each of which is incorporated by reference in its entirety for all purposes.

The circuitry shown in FIG. 6 is implemented in a WCD that provides defibrillation shocks in a manner like that described above. Battery 602 stores energy that is used by charger 604 to charge one or more capacitors in energy storage module 610 in preparation for delivering a defibrillation shock, as well as the other functions performed by the WCD. As above, battery 602 may be a rechargeable battery, a non-rechargeable battery, or a combination of rechargeable and non-rechargeable batteries.

Output circuit block 612 is illustrated as a switch for simplicity. However, output circuit block 612 can be implemented as an H-bridge in some embodiments. In addition, output circuit block 612 can include a relay or "main switch"

(not shown) that can close to allow (or open to prevent) charge flowing through the output circuit to patient 626.

Processor 606 is configured to detect shockable arrhythmias and determine if one or more other criteria are met. In response to an arrhythmia detection and meeting such other criteria, processor 606 is configured to control output circuitry to allow charge stored in energy storage module 610 to flow through to therapy electrodes 622 and 624, thereby delivering a defibrillation shock to patient 626. Processor 606 may also provide input to energy storage module to configure circuitry in the module and/or selectively activate a dump circuit in the module.

To generate pacing pulses using the same hardware used to deliver defibrillation shocks, in some embodiments software (e.g., instructions) for implementing charge rate control module 614 is loaded into a memory (not shown) of processor block 606 in FIG. 6. The Processor can be implemented using one or more processor and/or controller devices and is configurable (e.g., via execution of instructions) to implement the pacing and charge rate control modules to deliver pacing pulses in addition to the defibrillation functionality of a WCD.

In some embodiments, charge rate control module 614 employs PWM module 618 to provide pulse width modulated control signals to charger 604 to adjust the output of the charger. In embodiments using pulse width modulation, the processor 606 is configured (via execution of software including PMW module 618) to generate control signal(s) for the charger with a frequency and/or duty cycle that can be controlled (e.g., under programmed control).

In some embodiments, charger 604 is a constant energy charger. However, in some other embodiments, charger 604 may be a constant current charger, or may include both constant energy and constant current configurations to cover a range of impedances.

The charge rate control module can be omitted in some embodiments, using the charger to operate at a single rate.

Figure 7:
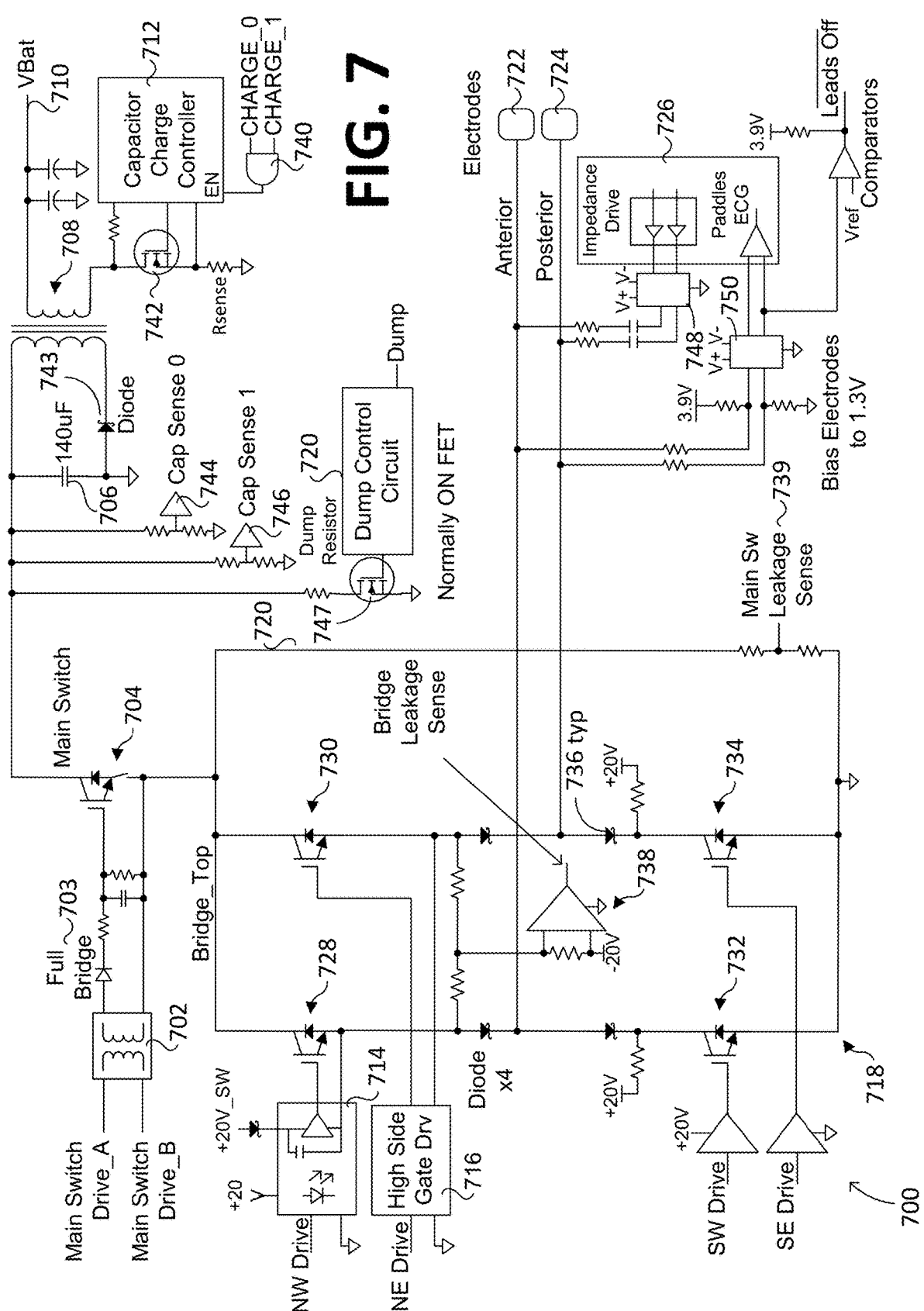
FIG. 7 is a schematic diagram of WCD circuitry shows configured to support various functionality, including generation of pacing pulses, associated with the embodiments disclosed herein.

FIG. 7 shows circuitry 700 configured to support various functionality, including generation of pacing pulses, associated with the embodiments disclosed herein. The higher level circuitry components and blocks include a transformer 702, a full bridge rectifier 703, a main switch 704, an energy storage module including a capacitor 706, a transformer 708, battery supply voltage 710 provided by a battery (not shown), a capacitor charge controller 712, high side gate drives 714 and 716, an H-bridge 718, a dump circuit including a dump circuit control 720 and FET 747, an anterior electrode 722, a posterior electrode 724, and an impedance drive 726. H-Bridge 718 includes four switches 728, 730, 732, and 734, and diodes 736. In one embodiment, main switch 704 and switches 728, 730, 732, and 734 are semiconductor switches (e.g., high voltage, high gain monolithic Bipolar MOS transistors. H-Bridge 718 also includes a bridge leakage sensor 738 configured to sense bridge leakage, and a main switch leakage sense 739 output. In some embodiments the dump circuit may be implemented in the H-Bridge (not separately shown herein).

Capacitor 706 is charged using battery supply voltage 710 using control input provided by capacitor charge controller 712, which is coupled to the low voltage side of transformer 708. In one embodiment, capacitor charge controller 712 comprises an Analog Devices® LT®3750 capacitor charge controller. A pair of control signals CHARGE_0 and CHARGE_1 are logically ANDed at AND gate 740, with the output of the AND gate provided as a charge enable (EN) input (corresponding to the CHARGE pin on the LT®3750 capacitor charge controller). Transformer 708 is used to increase battery supply voltage 710 using a switching output from capacitor charge controller 712 applied to a MOSFET 742. In one embodiment the transformer ratio is 1:30.6 (primary to secondary). The high voltage side of transformer 708 is coupled across capacitor 706 in a loop including a Diode 743; this creates a "flyback" configuration. In one embodiment, capacitor 706 is 140 uF at 1600-1700V.

A pair of capacitor sensors 744 and 746 (also labeled Cap Sense 0 and Cap Sense 1) are used to sense the charge level of capacitor 706. The dump circuits used to dump excess charge, and employs a semiconductor switch 747 in the illustrated embodiment (e.g., a depletion mode MOSFET).

Moving to the lower right-had corner of FIG. 7, the circuitry coupled to impedance drive 726 include a pair of clamp and EMI filters 748 and 750. In one embodiment, impedance drive 726 comprises an Analog Devices® ADAS1000 chip, which is a low power, 5-electrode ECG analog front end with respiration measurement and pace detection. As shown, a pair of inputs to the ADAS1000 chip comprises filtered signals for anterior electrode 722 and posterior electrode 724 (labeled as Paddles ECG).

The inputs to circuitry 700 include Main Switch Drive_A and Drive_B, NW Drive, NE Drive, SW Drive, and SE Drive, as well as a Dump input to dump circuit control 720 and CHARGE_0 and CHARGE_1 mentioned above. As described and illustrated in FIG. 9 below, all these inputs except for CHARGE_1 comprise digital output provided by a processor block 900.

FIG. 8 shows an example high side gate drive circuit 800, which can be used for high side gate drives 714 and 716, in one embodiment. High side gate drive circuit 800 receives a drive signal input 802 (e.g., NW Drive or NE Drive) at an amplifier 804 whose output is received as an input to an opto coupler 806. In one embodiment, opto coupler 806 comprises a Broadcom® ACPL-W343 Gate Drive Opto Coupler, noting this is merely an exemplary and non-limiting example of one of various opto couplers that may be used. Additional inputs include a 20V input and a 20V switched input. The outputs of bootstrap opto drive circuit 800 include $V_{OUT}$ 808 (which is used to drive a bridge switch) and $V_{EE}$ 810.

FIG. 9 shows a controller 900 that is implemented for processor block 606, in one embodiment. In one embodiment, controller 900 is a Texas Instruments® MSP430 microcontroller. Generally, such as shown in FIG. 9, a processor block may be implemented by a single IC or may employ an IC (e.g., controller, microcontroller, processor) coupled to a storage device and/or memory device. In the illustrated embodiment, controller 900 includes a processing element (microcontroller unit (MCU) 902), on-board Random Access Memory (RAM) 904, and on-board storage 906 (e.g., some type of non-volatile memory, such as but not limited to Flash memory. Generally, RAM 904 may comprise any type of Random Access Memory, such as DRAM, SRAM, SDRAM, etc.

As illustrated, controller 900 includes digital inputs, digital outputs, and Analog to Digital Conversion (ADC) signals. The digital inputs include the CHARGE_1 signal and a TRANSFER_ENERGY signal. The digital outputs include Main Switch Drive_A and Drive_B, NW, NE, SW, and SE (bridge) Drive signals, and the Dump and CHARGE_0 signals. The ADC signals include Cap Sense 0 and Cap Sense 1, Main Leakage, Bridge Leakage, VBAT Sense, and Supply Monitors.

Generally, software (e.g., compiled machine instructions), may be preinstalled in storage 906 or may be dynamically loaded during runtime operations. For example, original or new software (e.g., a software revision) may be loaded over the SPI (Serial Peripheral Interconnect) bus. During system boot, instructions in storage 906 will be loaded into RAM 904 for execution on MCU 902. As described elsewhere in here, in some embodiments the software is used to implement various functionality, such as software-based implementation of charge rate control module 618 and pacing module 616. In other embodiments, a combination of software and hardware (e.g., embedded logic) may be used to implement the functionality.

Charger as Current Source Embodiments

Under some embodiments the charger delivers pacing pulses. These embodiments may be suitable for patients with normal and low impedance. In some embodiments, for example, the charger is selected or designed to be capable of emulating a current source suitable for pacing when the impedance is low or moderate (e.g., less than 100Ω). In one non-limiting example, a 200 mA current source is emulated.

In some embodiments, the charger provides its output (without charging the capacitor between pulses) to serve as pacing pulses. In these embodiments, no impedance measurements are needed, and the charger energy output is fixed. For example, this could be the maximum charge output that the charger is capable of providing. In some embodiments a switch may be used to disconnect the capacitor from the charger output path.

Figure 7A:
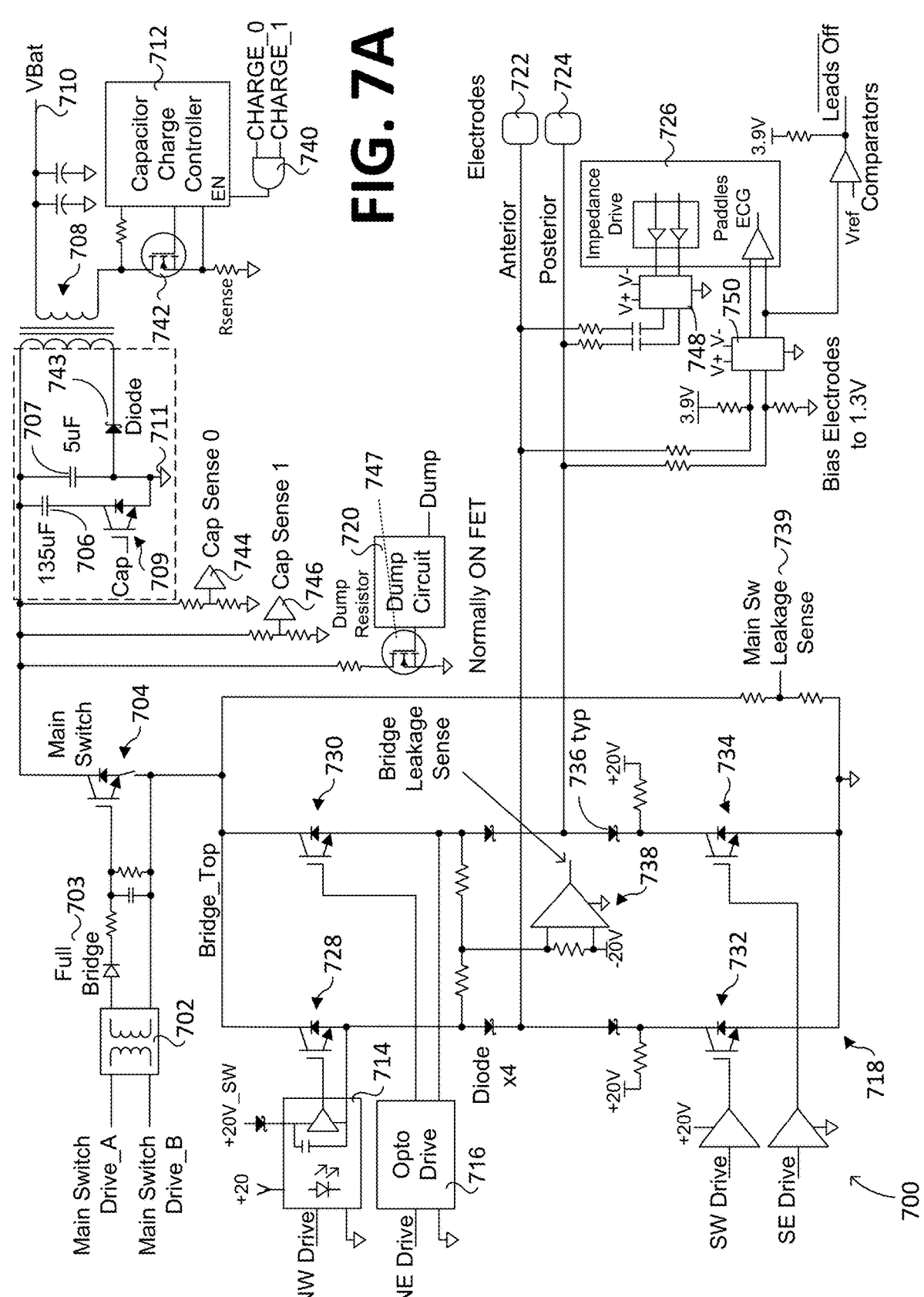
FIG. 7A is a schematic diagram illustrating an alternative configuration of FIG. 7 in which the circuitry coupling charge to the capacitor is modified.

For example, FIG. 7A shows an alternative configuration in which the circuitry coupling charge to the capacitor shown in the dashed box is modified (relative to the circuitry shown in FIG. 7) to enable capacitor 706 to be selectively disconnected from the charger output path. As shown, a new (left) branch has been added that includes a switch 709 coupled between capacitor 706 and ground 711. Meanwhile, in the original left-hand branch of FIG. 7 capacitor 706 has been replaced with a capacitor 707.

Switch 709 may be toggled using a "Cap" signal from controller 900 (which would now include an additional Cap digital output that is not shown in FIG. 9. The Cap signal and switch 709 is controlled by software executing on controller 900, or processor 606, in coordination with controlling the output of capacitor charge controller 712. Opening switch 709 disconnects the path from capacitor 706 to ground 711.

While the capacitor is not charged between pulses, the capacitor is charged during the pulse. Between pulses, the capacitor is disconnected (i.e., main switch 704 and switches 728, 730, 732, and 734 are not connecting the capacitor to the patient) and dump circuit is not active; with no significant drain on the capacitor relative to the duration between pacing pulses (e.g. a 1 s timescale), the capacitor voltage will remain approximately constant at the end of the end of one pacing pulse and through to the start of the next pacing pulse. When the equilibrium is reached, the capacitor is charged and the power is supplied from the charger during pulses (with the capacitor filtering out the charging pulses).

For illustrative purposes, an example of this not-charging-between-pulses scheme would be a patient that is 500 (and assume the equilibrium point is delivering 160 mA to the patient). During a pacing pulse, the charger is turned on and charges capacitor 706 in parallel with a 50Ω load. In this example we will assume the capacitor starts at 0V and charges by 2V by the end of that pulse. On the next pulse, the charger does the same action, but the capacitor starts charged to 2V; during this pulse, let's assume the charger charges to 6V. On the third pulse, the capacitor starts charged to 6V and charges to 8V halfway through the cycle and stays at 8V (this is the equilibrium point, where the energy from the charger is going to the 50Ω patient and not charging the capacitor any further (aside from the inter-cycle ripple)). On the fourth pulse, the capacitor starts charged to 8V and ends charged to 8V; the pulse is relatively flat due to this equilibrium point. Future pulses will behave in the same characteristic as this fourth pulse, of starting and ending with the capacitor charged to the same voltage. (It is noted that in some embodiments, the charger output is turned off during the impedance measurement, which causes a small discharge of the capacitor.)

The scheme also works if there is too high of a voltage (though these initial pulses will be a sort of exponential decay instead of a sort of exponential growth, until the equilibrium point is reached). However, it is preferably to avoid over charging, as the higher voltages also correlate to higher peak currents through the patient, which is more painful.

In some other embodiments, the initial pulses are generated using a default assumed impedance, with the impedance being measured at a selected point in the pulse. Based on the measured impedance, the energy output of the charger is adjusted by turning the charger on and off so that the desired output current is achieved. This may take several iterations as the relationship between energy output and output current for different impedances is difficult to determine. For example, the pacing module can be configured to determine the adjustments and in conjunction with the charge rate control module provide control signals to the charger to achieve the desired output current. In embodiments, the capacitor can be charged to a desired voltage and the charger controlled to maintain the capacitor voltage at a substantially constant level while the pacing pulses are generated.

In some embodiments, the charge rate control module is configured to use both PWM via hardware clocking (e.g., generated by the Processor or MCU) and higher level "gating" function performed by the software of the charge rate control module in controlling the hardware clocking. As previously mentioned, in some embodiments, the hardware clocking can be controlled for both frequency and duty cycle of the clock signals.

Figure 10:
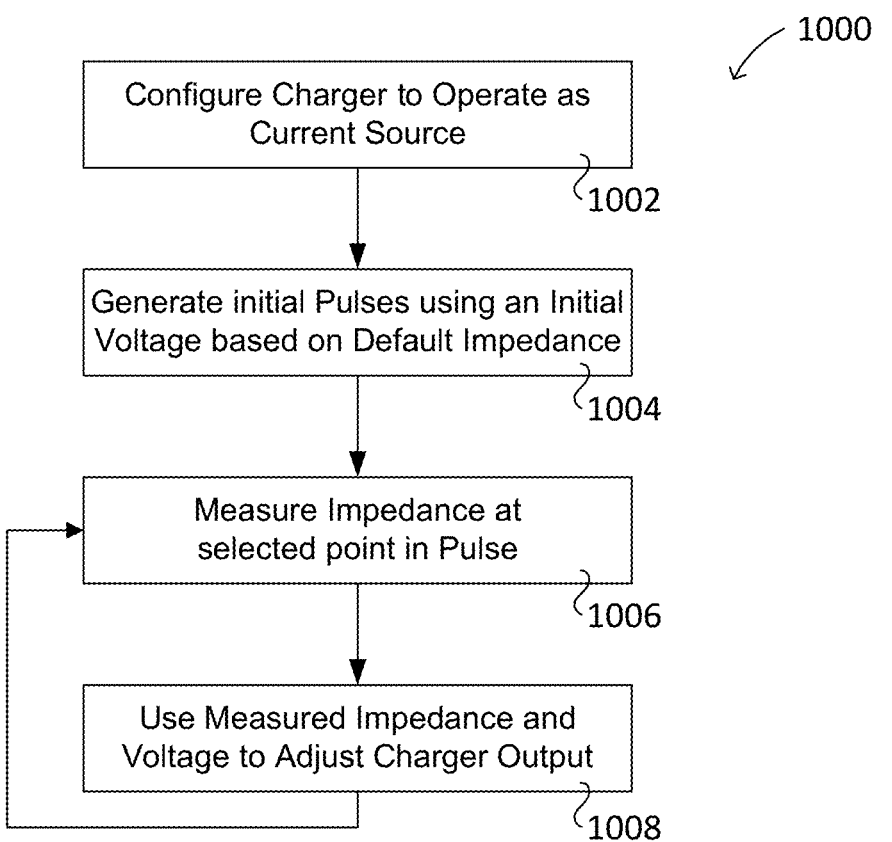
FIG. 10 is a flowchart illustrating operations and logic implemented for a pacing mode in which charger output is adjusted using impedance measurements, according to one embodiment.

As a further enhancement for some embodiments, the impedance may change over time while pacing pulses are delivered, and the Processor measures the impedance for adjustment of the charger output energy to achieve the desired output current. With reference to flowchart 1000 in FIG. 10, operation of the WCD in a mode supporting this functionality proceeds as follows. In a block 1002 the charger is configured to operate as a current source. This configuration operation may be performed via execution of software, with the operating mode selected via a user interface or the like. Optionally, the operation mode may be a default mode that does not involve any user or operator input.

In a block 1004 circuitry 700 is configured to generate initial pulses using an initial voltage based on a default impedance. The default impedance may be a predefined value in one embodiment, or may be a value that may be set by software via a user interface or the like.

As the initial pulses are generated, the impedance is measured at a selected point in the pulse, as depicted in a block 1006. During the impedance measurement, the output from capacitor charge controller 712 is disabled so as to not interfere with the impedance measurement. In some embodiments, the impedance can be measured using functionality built into impedance drive 726. In one non-limiting example, the Analog Devices® ADAS1000 chip used for impedance drive 726 provides a Thoracic impedance measurement function that may be used for the impedance measurement. Optionally, the impedance can be measured using techniques that are known in the art.

In a block 1008, the measured impedance and voltage is used to adjust the charger output.

$$V_{charge}=V_{lastpulse}+((R_{patient}*I_{targetcurrent})-V_{lastpulse}) \\ *ResponseFactor \qquad (1)$$

where $V_{lastpulse}$ is the measured voltage from the last delivered pulse (e.g., end of pulse voltage, maximum voltage, etc.), $R_{patient}$ is the impedance measured from 1006, $I_{targetcurrent}$ is the desired pacing current, and ResponseFactor is used to dampen the response (i.e. it is typically <1). The operations of blocks 1006 and 1008 may then be repeated until pacing pulses having a stable voltage and current are being generated, may be repeated on an ongoing basis, or utilized in other manners. For example, once a stable impedance is reached, a periodic check may be performed (e.g., once a minute) to detect if the impedance has changed, and if so, the operations of blocks 1006 and 1008 may be repeated until the impedance has stabilized. Alternatively, repeating the operations of blocks 1006 and 1008 on an ongoing basis will quickly detect changes in impedance and make appropriate changes.

Figure 11A:
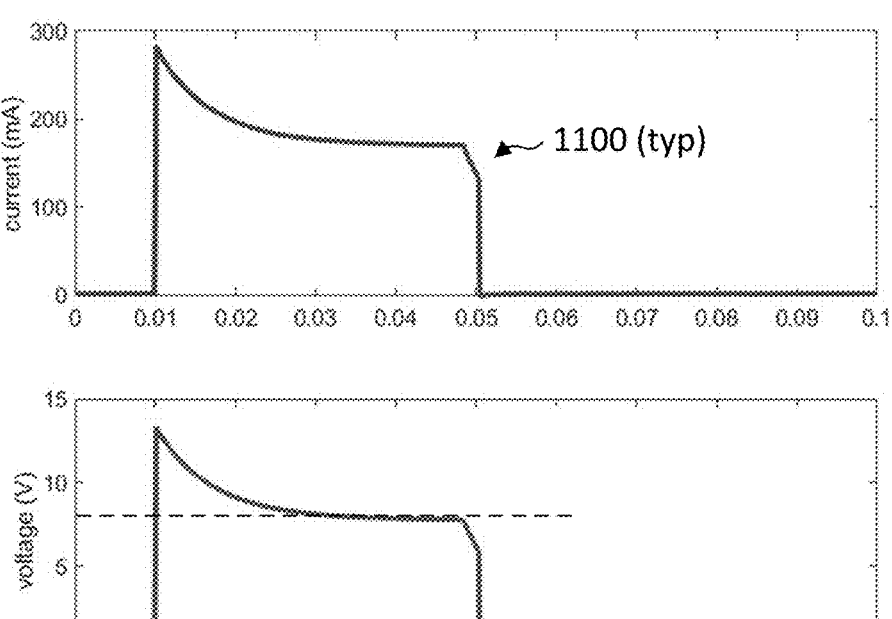
FIGS. 11A, 11B, and 11C show example waveforms of the first few pulses output by the WCD circuitry based on a 50Ω load with an initial charge voltage of ~15V.
Figure 11B:
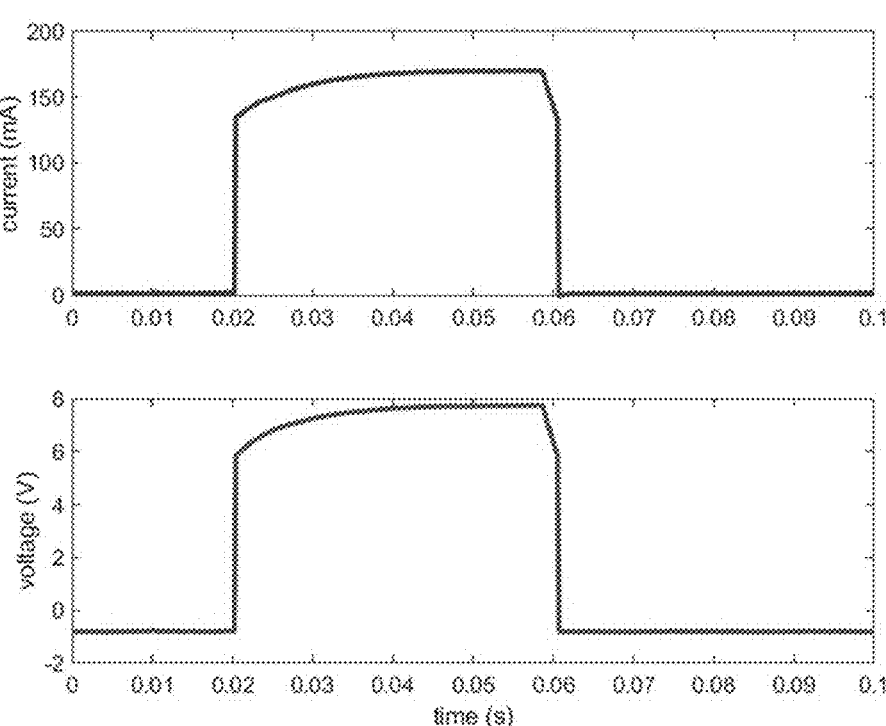
Figure 11C:
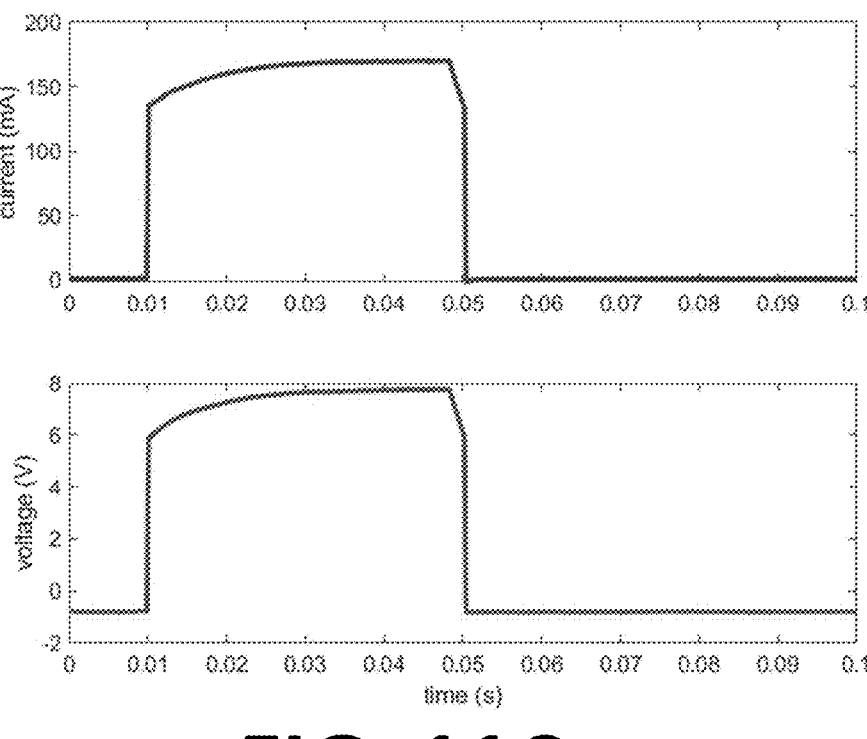

FIGS. 11A, 11B, and 11C show example waveforms of the first few pulses of a 50Ω load with an initial charge voltage of ~15V. In this case, the turn/dip 1100 in the waveforms occurs when the impedance is being measured (which involves turning the charger off). By the end of the first pulse (FIG. 11A), the impedance/voltage indicate a pre-charge isn't needed, so the next pulse charges a little during the start of the pulse, is relatively flat, then discharges while the impedance is being measured. This repeats for the third pulse (FIG. 11C); in this implementation using these parameters (50Ω load with an initial charge voltage of ~15V), there will always be a little charge at the start and discharge at the end of the pulses.

In an alternative embodiment, the voltage in block 1008 above may be replaced with a voltage characteristic of the pacing pulse waveform. For example, a measured or detected voltage characteristic of a pacing pulse may include a peak (highest) voltage, an average (e.g., average, RMS, median, etc.) voltage, or a voltage at a predetermined point in the pulse (e.g., middle, 75%, 90%, etc.).

Pacing Pulse Delivery

In some embodiments, the pacing pulses are delivered at a fixed, low rate (e.g., 40 bpm). In some other embodiments, the pacing pulses are delivered at a fixed, higher rate (e.g., 70 bpm). In still other embodiments, the pacing pulses are delivered at an oscillating rate profile designed to stimulate an intrinsic response (e.g., 70 bpm down to 40 bpm and back up to 70 bpm over a span of a few minutes). In some embodiments, this oscillating rate profile is the only pacing routine provided by the WCD. In some embodiments, the WCD is configured with only one of these pacing pulse delivery routines, while in others the WCD may be configured with multiple pacing routines that the Processor may select from depending on the detected arrhythmia.

Charger—Capacitor Embodiments

This is a hybrid of the previous embodiments above for high impedance patients. The charger-capacitor embodiments may be suitable for high impedance patients for which the charger (alone) is not able to provide the pacing pulses with the desired current. Thus, in these embodiments the capacitor is charged to a certain voltage level and allowed to discharge when the charger starts a pacing pulse. In some embodiments, the capacitor is charged to a level calculated (based on measured impedance) to achieve the desired output current in the pacing pulses.

The desired capacitor voltage can be determined by configuring the processor to measure impedance during the beginning of the pacing pulse, at the end of the pacing pulse, or any time during the pacing pulse, and then to calculate the appropriate capacitor voltage for the desired current (which can be preset, for example by entering settings via the UI of the WCD system). The processor is further configured to control the charger to maintain the capacitor voltage at the calculated level.

Generally, the resulting pacing pulse may not be rectangular if the charger cannot provide enough charge for pacing pulse because of the RC decay of the capacitor discharge. Accordingly, the charger, capacitor, and associated circuitry should be selected and configured to provide pacing pulses that reduce the RC decay. For example, the charger is implemented to have sufficient output capability so there is sufficient time between pulses for the charger to recharge the capacitor to the desired level.

Figure 12A:
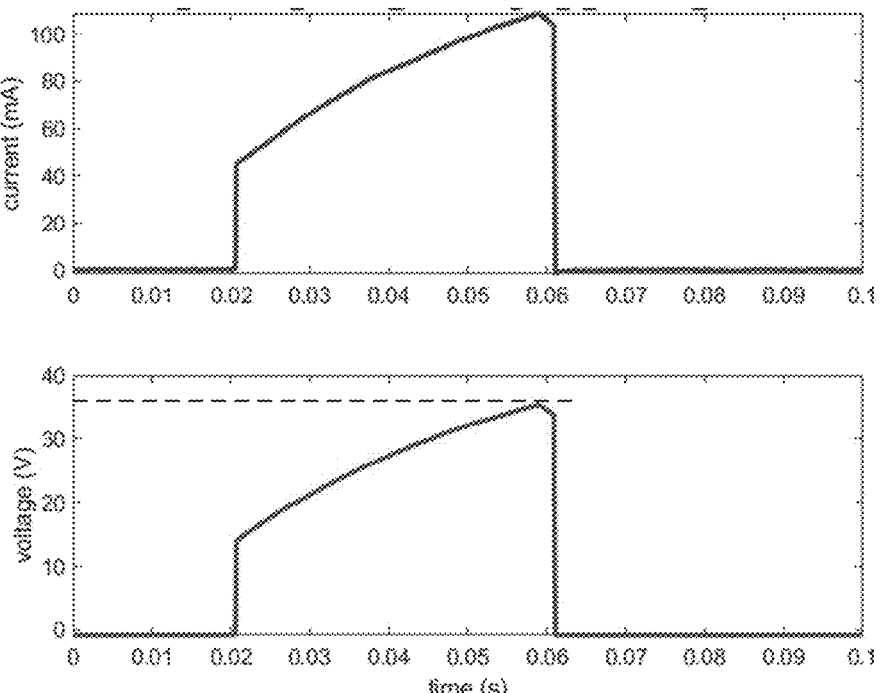
FIGS. 12A, 12B, and 12C show example waveforms of the first few pulses output by the WCD circuitry based on a 335Ω load with an initial charge voltage of 15V.
Figure 12B:
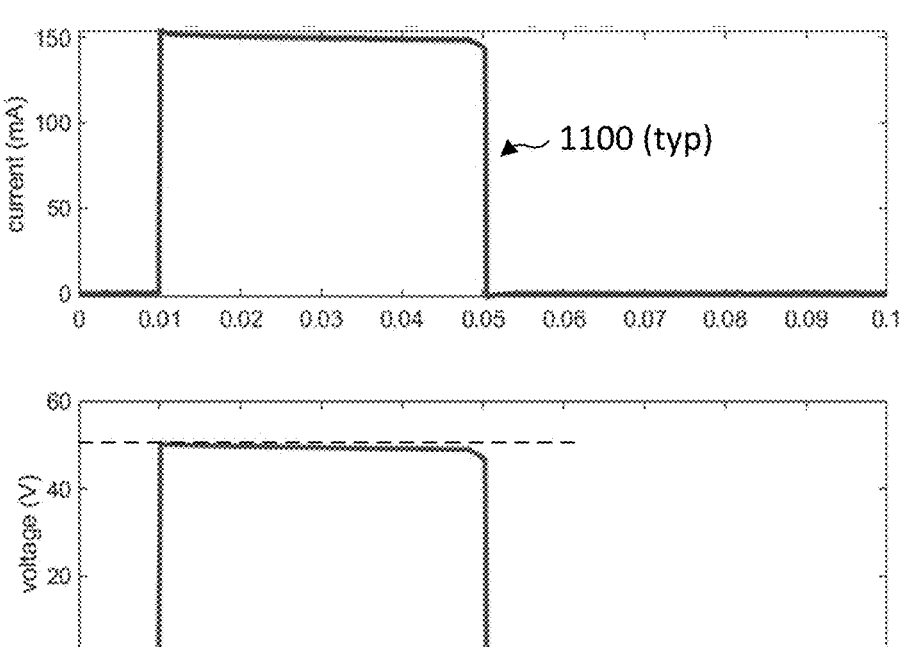
Figure 12C:
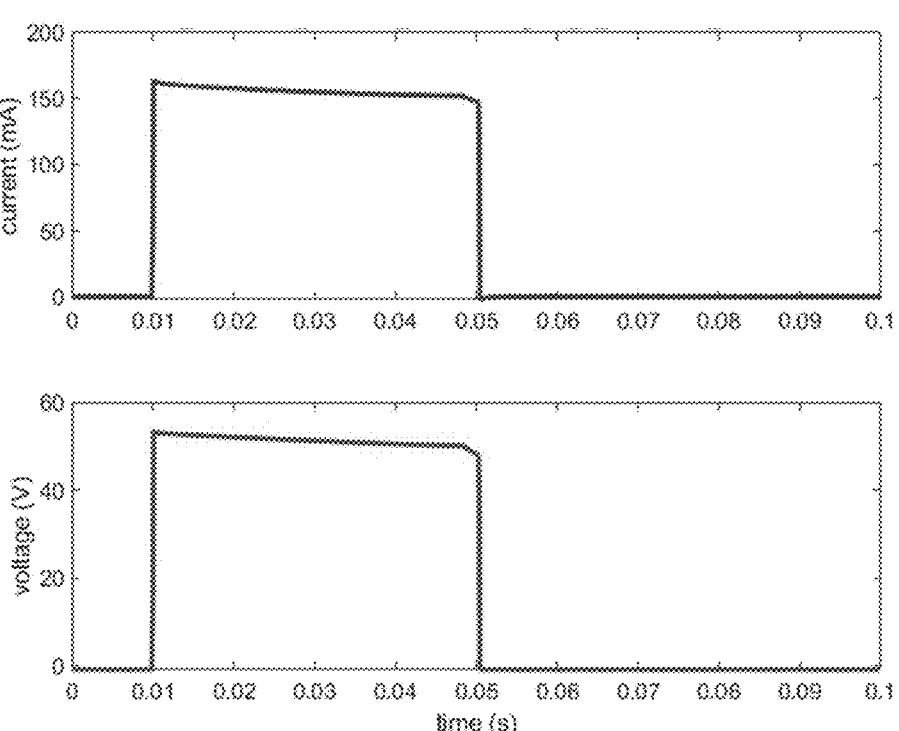

In cases where the patient impedance is higher (e.g., above 150 Ohms), the initial voltage will be adjusted. For illustrative purposes, FIGS. 12A, 12B, and 12C show example waveforms of the first three pulses of a 335Ω load with an initial charge voltage of 15V. As shown in FIG. 12A, the capacitor gets charged to approximately 35V by the end of the first pulse. The impedance/voltage/current measurement indicates a pre-charge is needed, so at the start of the second pulse (FIG. 12B), the voltage starts at ~50V (rather than ~35V). Then the impedance measurement at the end of the second pulse leads to a slightly higher initial charge voltage in the third waveform (FIG. 12C).

Charger—Capacitor—Output Circuit Embodiments

This is a modification of previous embodiments above in which the output circuit is controlled via PWM to "feather" the pulse output (at least in the initial part of the pulse) to avoid large spikes on the leading edge of the pulse. The Processor (e.g., the charge rate control module) is configured to control one or more switches in the output path, for example by gradually turning one or more of these switches on to slow the leading edge of the pacing pulse. In some embodiments, the main switch can be controlled as described above. But in other embodiments, in addition to or instead of the main switch, one or more other switches in the H-bridge can be controlled to control the shape of the leading edge of the pacing pulses.

Output Circuit Switch(s) in Linear Mode Embodiments

In these embodiments, the processor is configured to operate one or more of the transistor switches of the output circuit in the linear region rather than driving it to be either OFF or in saturation as is done in currently available WCDs. In some embodiments, the switch(s) operated in the linear mode could be the main switch. In other embodiments, in addition to or instead of the main switch, one or more other switches in the H-bridge can be controlled to operate in the linear mode. Example WCDs implementing such embodiments include those in which the main switch of the output circuit is a transistor rather than a relay. Such embodiments may have the advantage that the output current of the entire circuit can be controlled by changing the impedance of the main switch to emulate a current source with the desired current level for pacing.

In some embodiments, the processor is configured to control the gate voltage of the switch (or switches) via PWM. For example, one or more of the Main Switch Drive_A and Drive_B, NW, NE, SW, and SE (bridge) Drive signals in FIG. 9 may comprise a PWM signal rather than an On/Off signal.

In some embodiments, the processor is configured to operate a semiconductor switch in the linear/ohmic region with an amount of overhead voltage on the capacitor. For the overhead voltage, the capacitor is charged to a voltage high enough to guarantee that the desired current can be maintained during the full pulse width. The overhead voltage can be calculated as, $$V_{overhead} = I_{target\_current} * t_{pulse\_duration} / CHV\_cap \qquad (2)$$

In an example implementation, with a 200 mA target current, a 40 ms pulse duration and a 140 μF capacitor, the overhead voltage would be 57V.

Figure 13:
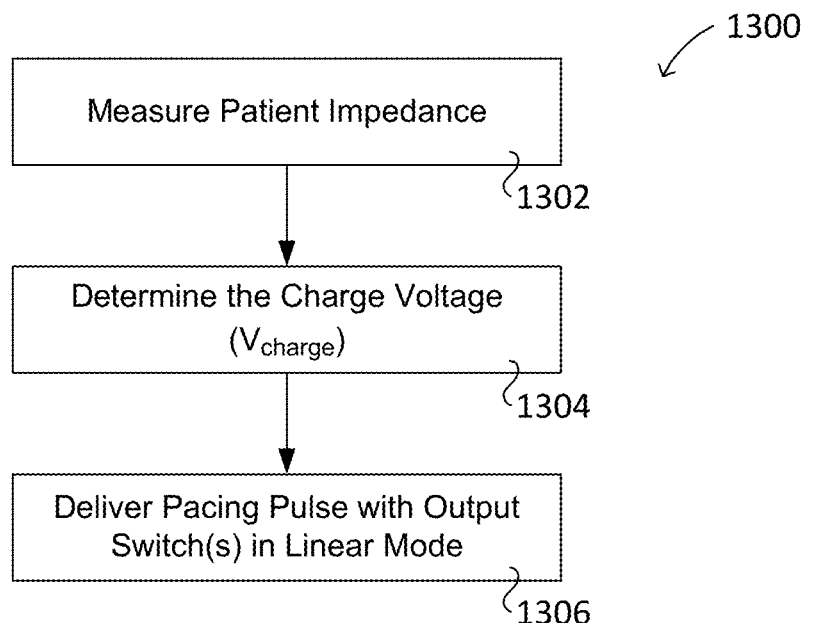
FIG. 13 is a flowchart illustrating operations used in a WCD pacing mode under which one or more output circuit switches are implemented in a linear mode.

With reference to flowchart 1300 in FIG. 13, the processor is configured to determine the final charge voltage in some embodiments as follows. In a block 1302 the patient impedance is measured. In some embodiments an external circuit that can measure patient impedance is used. In other embodiments, the processor is configured to cause a test shock to be delivered and to measure impedance based on the waveform parameters.

Next, in a block 1304 the charge voltage $V_{charge}$ is determined as, $$V_{charge} = R_{patient} * I_{target\_current} + V_{overhead} + V_{parasitics} \qquad (2)$$

Parasitics are design dependent and include any losses in the power path that may affect the delivered current. $R_{patient} * I_{target\_current}$ is the minimum voltage needed to support the target current at the end of the pacing pulse.

In a block 1306 the pacing pulse is delivered with one or more output switches in the linear mode, as described above.

Some additional design considerations include the following. This overhead voltage will be absorbed by the linear/ohmic switches, so the switches are selected to be able to withstand the energy. The energy delivered will be a decaying exponential voltage with a constant current. By using multiple switches in a linear/ohmic mode, the absorbed energy per device can be reduced.

PWM Implements

As discussed above, pulse width modulation may be implemented in software, in hardware, or using a combination of hardware and software. An example of PWM being implemented in hardware would be a hardware component, such as a chip, with programmable PWM functionality (e.g., either a standalone chip or a multifunction chip). An example of a software-based implementation is using software that is executed on one or more processing elements such as a CPU, processor, processor core, processing element in a microcontroller, etc. As will be recognized by those skilled in the art, software (e.g., machine instructions compiled from source code, byte code, etc.) cannot perform any functions without being executed on some form of hardware; however, it is also recognized in the computer arts that functionality that is implemented via execution of software is considered software-based functionality, which applies to the following embodiment.

FIG. 14 shows a table 1400 that is used in one embodiment to vary the duty cycle of a digital output, such as used to enable the charger output. Table 1400 can be implemented in software using known techniques, such as a data structure (e.g., array). As shown there are 16 columns used to store respective binary values ('1' or '0') that correspond to whether the output digital signal is High ('1', representing on) or Low ('0', representing off). For example, the pattern for Pace Pulse Option Value 10 is 1 1 0 1 1 0 1 1 0 1 1 0 1 0 1 0, which results in a 62.5% duty cycle. In the illustrated example, the duration of each entry is 200 microseconds (uS). This value is exemplary and non-limiting, as other time duration values may be used.

Generally, the processor hardware will either include one or more built-in timers and/or provide machine instructions or libraries that enable software execution on the processor hardware to access the timers. Logic that is implemented in software can determine what duty cycle and time duration per entry to apply to adjust the waveform of the digital output used as an input to emulate an analog PWM output from PWM circuit or the like. Such digital PWM signals may be used to drive the charger and/or may be used to drive one or more switches.

Selection of Pacing Pulse Profile for Detected Arrhythmias

Figure 15:
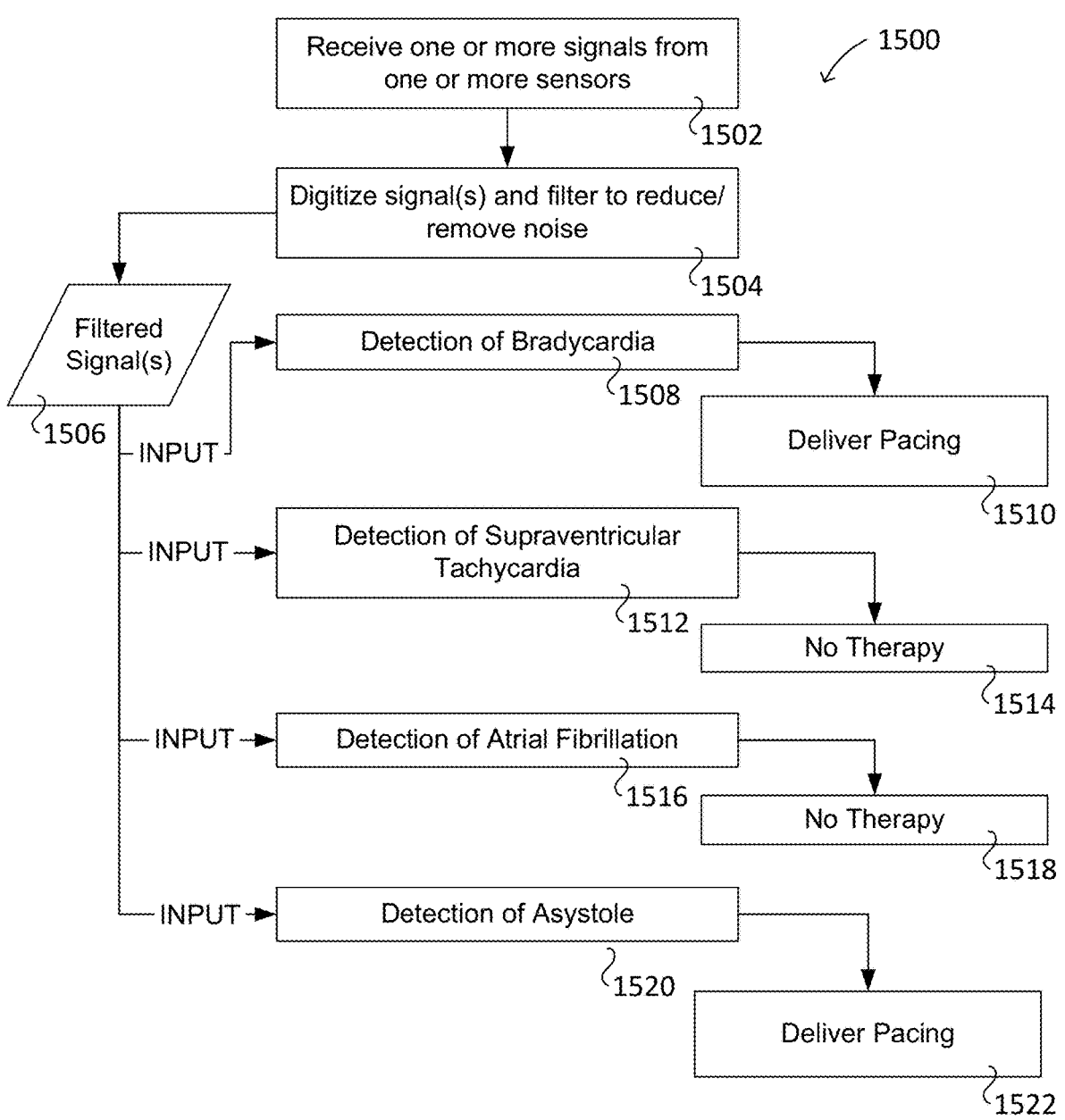
FIG. 15 is a flowchart illustrating operations to detect arrhythmias and select pacing pulse profiles based on a detected arrhythmia, according to one embodiment.

FIG. 15 shows a flowchart 1500 illustrating operations to detect arrhythmias and select pacing pulse profiles based on a detected arrhythmia, according to one embodiment. The process begins in a block 1502 with signals being received from one or more sensors attached (or otherwise electrically) coupled to the ambulatory patient. In a block 1504 the signals, which generally will comprise analog signals, are digitized (e.g., using Analog-to-Digital conversion (ADC) circuitry). In block 1504 the signals are also filtered to reduce and/or remove noise. Filtering can be done using analog or digital filtering using known techniques such as disclosed in U.S. Pat. Nos. 9,592,403, 9,757,581, 10,918, 879, and 11,103,717 referenced above.

The output of block 1504 is filtered signal(s) 1506, which are used as input to detect various types of arrhythmias. In a block 1508 Bradycardia arrhythmias are detected. Bradycardia is a resting heart rate this is slower than 60 beats per minute. This may be a natural condition for some people who are young and/or physically fit. Bradycardia may be detected using a heart rate threshold. In one embodiment, the software UI for the WCD includes an option to change the Bradycardia threshold (from nominally 60 bpm) to another value or to disable detection of Bradycardia. If Bradycardia is enabled and detection, the logic proceeds to a block 1510 in which a pacing pulse is delivered. For example, an 80 bpm pacing pulse frequency might be used with a target current of 160 mA.

In a block 1512 supraventricular tachycardia is detected. Supraventricular tachycardia is an irregularly fast heartbeat that develops when the normal electrical impulses of the heart are disrupted. In one embodiment, techniques disclosed in U.S. Patent Publication No. 2021/0052181 are utilized to detect supraventricular tachycardia. When supraventricular tachycardia is detected, the logic proceeds to a block 1514 in which no therapy is applicable.

In a block 1516 atrial fibrillation is detected. Atrial fibrillation, also known as A-fib, is a condition that causes irregular and fast heartbeat, but is distinguishable from supraventricular tachycardia. In one embodiment, techniques disclosed in U.S. Pat. Pub. No. 2021/0052181 are utilized to detect atrial fibrillation. When atrial fibrillation is detected, the logic proceeds to a block 1518 in which no therapy is applicable.

In a block 1520 Asystole arrhythmias are detected. Asystole is the cessation of electrical and mechanical activity of the heart. Asystole may be detected using a heart rate threshold. In one embodiment, the software UI for the WCD includes an option to change the Asystole threshold (from nominally a 20 s pause) to another value. When Asystole is detected, the logic proceeds to a block 1522 in which a pacing pulse is delivered. For example, an 80 bpm pacing pulse frequency might be used with a target current of 160 mA.

Generally, detection of one or more of the aforementioned arrhythmias may be performed on an ongoing basis or periodically. In some embodiments, the UI for the WCD software provides one or more settings for enabling detection of selected arrhythmias and (optionally) to tune detection parameters. As discussed above, the WCD may provide motion detection capabilities. Motion detection may be combined with arrhythmias detection to selectively enable detection of some arrhythmias. For example, exercise may result in elevated heartrates that are not related to an arrhythmia.

Although some embodiments have been described in reference to particular implementations, other implementations are possible according to some embodiments. Additionally, the arrangement and/or order of elements or other features illustrated in the drawings and/or described herein need not be arranged in the particular way illustrated and described. Many other arrangements are possible according to some embodiments.

The circuitry and associated circuit elements illustrated and described herein are exemplary and non-limiting. Those having skill in the art with recognize components made by the same or other vendors may be implemented in place of the components illustrated in the Figures and that the values for circuit elements such as resistor, capacitor, switches, and voltages are exemplary and non-limiting.

In each system shown in a Figure, the elements in some cases may each have the same reference number or a different reference number to suggest that the elements represented could be different and/or similar. However, an element may be flexible enough to have different implementations and work with some or all of the systems shown or described herein. The various elements shown in the figures may be the same or different. Which one is referred to as a first element and which is called a second element is arbitrary.

In the description and claims, the terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still co-operate or interact with each other. Additionally, "communicatively coupled" means that two or more elements that may or may not be in direct contact with each other, are enabled to communicate with each other. For example, if component A is connected to component B, which in turn is connected to component C, component A may be communicatively coupled to component C using component B as an intermediary component.

An embodiment is an implementation or example of the inventions. Reference in the specification to "an embodiment," "one embodiment," "some embodiments," or "other embodiments" means that a particular feature, structure, or characteristic described in connection with the embodiments is included in at least some embodiments, but not necessarily all embodiments, of the inventions. The various appearances "an embodiment," "one embodiment," or "some embodiments" are not necessarily all referring to the same embodiments.

Not all components, features, structures, characteristics, etc. described and illustrated herein need be included in a particular embodiment or embodiments. If the specification states a component, feature, structure, or characteristic "may", "might", "can" or "could" be included, for example, that particular component, feature, structure, or characteristic is not required to be included. If the specification or claim refers to "a" or "an" element, that does not mean there is only one of the element. If the specification or claims refer to "an additional" element, that does not preclude there being more than one of the additional elements.

An algorithm is here, and generally, considered to be a self-consistent sequence of acts or operations leading to a desired result. These include physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers or the like. It should be understood, however, that all of these and similar terms are to be associated with the appropriate physical quantities and are merely convenient labels applied to these quantities.

As discussed above, various aspects of the embodiments herein may be facilitated by corresponding software and/or firmware components and applications, such as software and/or firmware executed by an embedded processor or the like. Thus, embodiments of this invention may be used as or to support a software program, software modules, firmware, and/or distributed software executed upon some form of processor, processing core or embedded logic a virtual machine running on a processor or core or otherwise implemented or realized upon or within a non-transitory computer-readable or machine-readable storage medium. A non-transitory computer-readable or machine-readable storage medium includes any mechanism for storing or transmitting information in a form readable by a machine (e.g., a computer). For example, a non-transitory computer-readable or machine-readable storage medium includes any mechanism that provides (i.e., stores and/or transmits) information in a form accessible by a computer or computing machine (e.g., computing device, electronic system, etc.), such as recordable/non-recordable media (e.g., read only memory (ROM), random access memory (RAM), magnetic disk storage media, optical storage media, flash memory devices, etc.). The content may be directly executable ("object" or "executable" form), source code, or difference code ("delta" or "patch" code). A non-transitory computer-readable or machine-readable storage medium may also include a storage or database from which content can be downloaded. The non-transitory computer-readable or machine-readable storage medium may also include a device or product having content stored thereon at a time of sale or delivery. Thus, delivering a device with stored content, or offering content for download over a communication medium may be understood as providing an article of manufacture comprising a non-transitory computer-readable or machine-readable storage medium with such content described herein.

The operations and functions performed by various components described herein may be implemented by software running on a processing element, via embedded hardware or the like, or any combination of hardware and software. Such components may be implemented as software modules, hardware modules, special-purpose hardware (e.g., application specific hardware, ASICs, DSPs, etc.), embedded controllers, hardwired circuitry, hardware logic, etc. Software content (e.g., data, instructions, configuration information, etc.) may be provided via an article of manufacture including non-transitory computer-readable or machine-readable storage medium, which provides content that represents instructions that can be executed. The content may result in a computer performing various functions/operations described herein.

As used herein, a list of items joined by the term "at least one of" can mean any combination of the listed terms. For example, the phrase "at least one of A, B or C" can mean A; B; C; A and B; A and C; B and C; or A, B and C.

The above description of illustrated embodiments of the invention, including what is described in the Abstract, is not intended to be exhaustive or to limit the invention to the precise forms disclosed. While specific embodiments of, and examples for, the invention are described herein for illustrative purposes, various equivalent modifications are possible within the scope of the invention, as those skilled in the relevant art will recognize.

These modifications can be made to the invention in light of the above detailed description. The terms used in the following claims should not be construed to limit the invention to the specific embodiments disclosed in the specification and the drawings. Rather, the scope of the invention is to be determined entirely by the following claims, which are to be construed in accordance with established doctrines of claim interpretation.

What is claimed is:

1. A wearable cardioverter defibrillator (WCD) for an ambulatory patient, comprising:

a support structure configured to be worn by the ambulatory patient;

WCD circuitry, operatively coupled to the support structure, including, a power source;

a charger, coupled to the power source;

an energy storage module, operatively coupled to the charger; and output circuitry, coupled to the energy storage module;

first and second therapy electrodes coupled to the output circuitry and configured to be maintained on a body of the ambulatory patient when the support structure is worn by the ambulatory patient; and control circuitry operatively coupled to the charger, the energy storage module, and the output circuitry, the control circuitry configured to cause the WCD circuitry to emulate a current source with an adjustable current level to generate pacing pulses delivered to the first and second therapy electrodes.

2. The WCD of claim 1, further comprising:

at least one sensor configured to sense a parameter of the ambulatory patient; and a measurement circuit, operatively coupled to the at least one sensor and the control circuitry and configured to render a patient input responsive to the sensed parameter, wherein the control circuitry is configured to detect arrhythmias that are treated with the pacing pulses and control when the pacing pulses are delivered to the first and second therapy electrodes.

3. The WCD of claim 2, wherein the control circuitry includes:

one or more processors; and one or more software modules comprising instructions configured to be executed on at least one of the one or more processors to implement control functions including generating the pacing pulses.

4. The WCD of claim 3, wherein the one or more software modules include a pacing module configured to receive one or more sensed parameters from the measurement circuit, detect arrhythmias treated with the pacing pulses, and provide control input to the output circuitry to control timing of the pacing pulses.

5. The WCD of claim 3, wherein the one or more software modules include a charge rate control module comprising instructions to, upon execution on a processor of the one or more processors, control charging of the energy storage module.

6. The WCD of claim 5, further comprising a pulse width modulation (PWM) module implemented in at least one of software and hardware, wherein the PWM module is configured to provide a PWM control signal to the charger.

7. The WCD of claim 6, wherein the PWM control signal comprises a pacing signal to cause the charger to generate the pacing pulses, and wherein at least one of a frequency and duty cycle of the PWM control signal is programmatically controlled in software.

8. The WCD of claim 1, wherein the WCD circuitry is configured to:

initiate generation of pacing pulses having a voltage level;

measure an impedance load of the ambulatory patient; and adjust the voltage level of the pacing pulses using the measured impedance load.

9. The WCD of claim 1, wherein the WCD circuitry is configured to:

generate one or more defibrillator shocks to the ambulatory patient; and perform post shock pacing during which the pacing pulses are delivered to the ambulatory patient via the first and second therapy electrodes.

10. The WCD of claim 1, wherein the charger includes at least one of constant energy and constant current configurations to cover a range of impedances.

11. An apparatus, including circuitry comprising:

an energy storage module;

a charger, configured to be coupled to a battery and provide a charge to the energy storage module, an output circuit block, operatively coupled to the charger and the energy storage module, the output circuit block having at least one output configured to be coupled to first and second therapy electrodes;

a processor block, operatively couple to the charger, the energy storage module, and the output circuit block, the processor block including one or more processing elements on which instructions are executed and at least one memory in which the instructions are stored; and one or more software modules comprising the instructions configured to be executed by at least one of the one or more processing elements to enable the apparatus that includes the circuitry to emulate a current source with an adjustable current level to generate pacing pulses delivered to the first and second therapy electrodes, wherein the apparatus is further configured to:

initiate generation of pacing pulses having a voltage level;

measure an impedance load of an ambulatory patient; and adjust the voltage level of the pacing pulses using the measured impedance load.

12. The apparatus of claim 11, wherein the output circuit block includes:

a bridge configured to receive four drive signals output from the processor block; and an impedance drive, coupled to a pair of outputs from the bridge, the pair of outputs configured to be coupled to the first and second therapy electrodes.

13. The apparatus of claim 11, wherein the apparatus is configured to be implemented in a wearable cardioverter defibrillator (WCD) for an ambulatory patient, the WCD including at least one sensor configured to sense a parameter of the ambulatory patient, the apparatus further comprising a measurement circuit, operatively coupled to the at least one sensor and providing one or more sensor inputs to the processing block, and wherein execution of the instructions enables the apparatus to detect arrhythmias of the ambulatory patient that are treated with the pacing pulses and control when the pacing pulses are delivered to the first and second therapy electrodes.

14. The apparatus of claim 11, wherein the apparatus is further configured to:

measure a voltage characteristic of a pacing pulse; and use the voltage characteristic as a parameter to adjust the voltage level of a next pacing pulse.

15. The apparatus of claim 11, further comprising a pulse width modulation (PWM) module implemented in at least one of software and hardware, wherein the PWM module is configured to provide a PWM control signal to the charger.

16. The apparatus of claim 11, wherein the energy storage module includes a capacitor, and wherein execution of the instructions enables the apparatus to generate the pacing pulses delivered to the first and second therapy electrodes in a manner that does not charge the capacitor between pulses.

17. A method implemented by a wearable cardioverter defibrillator (WCD) worn by an ambulatory patient, the WCD including a battery coupled to WCD circuitry including a charger, an energy storage module, control circuitry, and output circuitry coupled to first and second therapy electrodes in contact with the ambulatory patient, the method comprising:

controlling the charger with the control circuitry to emulate a current source;

outputting pacing pulses to the first and second therapy electrodes without the current source;

initiating generation of pacing pulses having a voltage level;

measuring an impedance load of the ambulatory patient; and adjusting the voltage level of the pacing pulses using the measured impedance load.

18. The method of claim 17, wherein the charger is a constant energy charger, further comprising emulating the current source with the constant energy charger.

19. The method of claim 17, wherein the control circuitry includes one or more processing elements, further comprising executing software instructions on at least one processing element of the one or more processing elements to generate control signals to the control operation of the charger.

20. The method of claim 17, wherein the WCD includes one or more sensors, the method further comprising:

receiving one or more signals from the one or more sensors;

determining the impedance load based on the one or more signals that are received; and adjusting the pacing pulses to deliver pacing pulses having a desired current.

21. The method of claim 17, further comprising:

measuring a voltage characteristic of a pacing pulse; and using the voltage characteristic as a parameter to adjust the voltage level of a next pacing pulse.

22. The method of claim 17, wherein the energy storage module comprises a capacitor, the method further comprising employing the charger to provide an output without charging the capacitor between pulses.

23. The method of claim 17, wherein the WCD includes one or more sensors, the method further comprising:

receiving one or more signals from the one or more sensors;

processing the one or more signals to detect an arrhythmia, and in response thereto, implementing a pacing routing from among multiple pacing routines based on the detected arrhythmia.

\*    \*    \*    \*    \*